(12) United States Patent
Burke et al.

(10) Patent No.: US 9,738,677 B2
(45) Date of Patent: Aug. 22, 2017

(54) AMPHOTERICIN B DERIVATIVE WITH REDUCED TOXICITY

(71) Applicant: The Board of Trustees of the University of Illinois, Urbana, IL (US)

(72) Inventors: Martin D. Burke, Champaign, IL (US); Brice E. Uno, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/310,815

(22) PCT Filed: May 15, 2015

(86) PCT No.: PCT/US2015/030965
§ 371 (c)(1),
(2) Date: Nov. 14, 2016

(87) PCT Pub. No.: WO2015/175875
PCT Pub. Date: Nov. 19, 2015

(65) Prior Publication Data
US 2017/0088572 A1    Mar. 30, 2017

Related U.S. Application Data

(60) Provisional application No. 62/045,907, filed on Sep. 4, 2014, provisional application No. 61/994,450, filed on May 16, 2014.

(51) Int. Cl.
C07H 17/08 (2006.01)
A61K 9/00 (2006.01)
A61K 31/7048 (2006.01)

(52) U.S. Cl.
CPC ............ *C07H 17/08* (2013.01); *A61K 9/0014* (2013.01); *A61K 9/0019* (2013.01); *A61K 9/0053* (2013.01); *A61K 31/7048* (2013.01)

(58) Field of Classification Search
None
See application file for complete search history.

(56) References Cited

U.S. PATENT DOCUMENTS

2004/0242505 A1    12/2004    Kaniga
2007/0123477 A1    5/2007    Malcolmson et al.

OTHER PUBLICATIONS

Croatt et al., Organic Letters, 2011, vol. 13, No. 6, 1390-1393.*
Croatt, Mitchell P. et al., "Probing the Role of the Mycosamine C2'—OH on the Activity of Amphotericin B," Organic Letters 2011, vol. 13, No. 6, 1390-1393.
Wilcock, Brandon C., et al. "C2'—OH of Amphotericin B Plays an Important Role in Binding the Primary Sterol of Human Cells but Not Yeast Cells," Journal of the American Chemical Society, 2013 Jun. 12, vol. 135(23), pp. 8488-8491.
International Search Report dated Jul. 28, 2015 from corresponding application No. PCT/US2015/030965.

* cited by examiner

*Primary Examiner* — Traviss C McIntosh, III
(74) *Attorney, Agent, or Firm* — Dana M. Gordon; Foley Hoag LLP

(57) ABSTRACT

Disclosed is a derivative of amphotericin B (AmB), denoted C2'epiAmB, with an improved therapeutic index over amphotericin B, pharmaceutical compositions comprising the AmB derivative, methods of making the AmB derivative and the pharmaceutical composition, and their use in methods of inhibiting growth of a yeast or fungus and treating a yeast or fungal infection. C2'epiAmB is an epimer of the parent compound. Specifically, C2'epiAmB differs from the parent compound at the C2' stereogenic center on mycosamine. This difference in structure results in (i) retained capacity to bind ergosterol and inhibit growth of yeast, (ii) greatly reduced capacity to bind cholesterol, and (iii) essentially no toxicity to human cells.

9 Claims, 9 Drawing Sheets

C2'epiAmE

FIG. 5

|  |  | AmB | C2'deOAmB | C2'epiAmB |
|---|---|---|---|---|
| ITC binding | Erg | Yes | Yes | Yes |
|  | Chol | Yes | No | No |
| MIC (μM) | *S. cerevisiae* | 0.5 | 1 | 2 |
|  | *C. albicans* | 0.25 | 1 | 2 |
| MHC (μM) | RBC | 8.5 | > 500 | > 500 |
| MTC (μM) | REC | 2.4 | > 80 | > 80 |

AMPHOTERICIN B DERIVATIVE WITH REDUCED TOXICITY

RELATED APPLICATIONS

This application is a §371 national stage application based on Patent Cooperation Treaty Application serial number PCT/US2015/030965, filed May 15, 2015, which claims benefit of priority to U.S. Provisional Patent Application No. 61/994,450, filed May 16, 2014, and U.S. Provisional Patent Application No. 62/045,907, filed Sep. 4, 2014.

GOVERNMENT SUPPORT

This invention was made with government support under Grant No. GM080436 awarded by the National Institutes of Health. The government has certain rights in the invention.

BACKGROUND OF THE INVENTION

The polyene macrolide natural product amphotericin B (AmB) is the archetype for both small molecules that form ion channels in living cells[1] and antibiotics that are inherently refractory to microbial resistance.[2] AmB is also, unfortunately, highly toxic,[3] which often limits its effective utilization as the last line of defense against life-threatening systemic fungal infections. Because both the incidence of such fungal infections and resistance to all other classes of antifungals are on the rise,[2] finding a way to improve the therapeutic index of AmB has become an increasingly important problem. Some progress has been made with liposomal formulations, but they are often prohibitively expensive,[4] and substantial toxicity still remains.[5] Despite 50 years of extensive efforts worldwide, a clinically viable derivative of AmB with an improved therapeutic index has yet to emerge.[6]

SUMMARY OF THE INVENTION

An aspect of the invention is C2'epiAmB, represented by

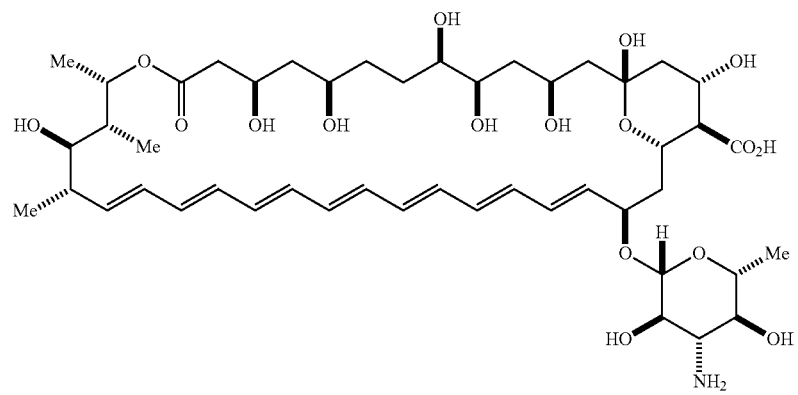

or a pharmaceutically acceptable salt thereof.

An aspect of the invention is a pharmaceutical composition, comprising C2'epiAmB, represented by

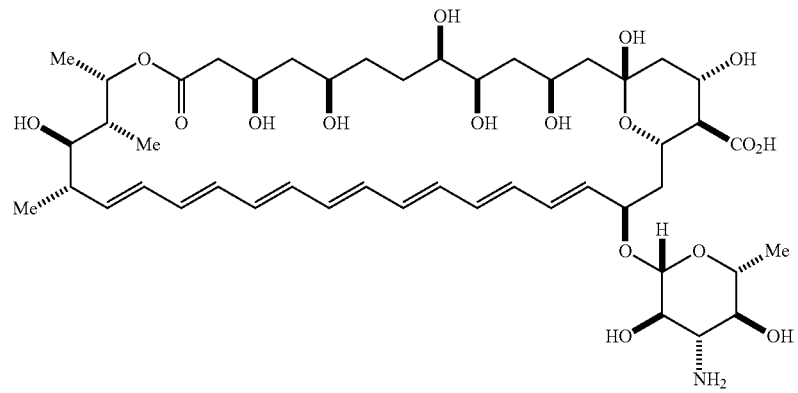

or a pharmaceutically acceptable salt thereof; and a pharmaceutically acceptable carrier.

An aspect of the invention is a method of inhibiting growth of a yeast or fungus, comprising contacting the yeast or fungus with an effective amount of C2'epiAmB, represented by

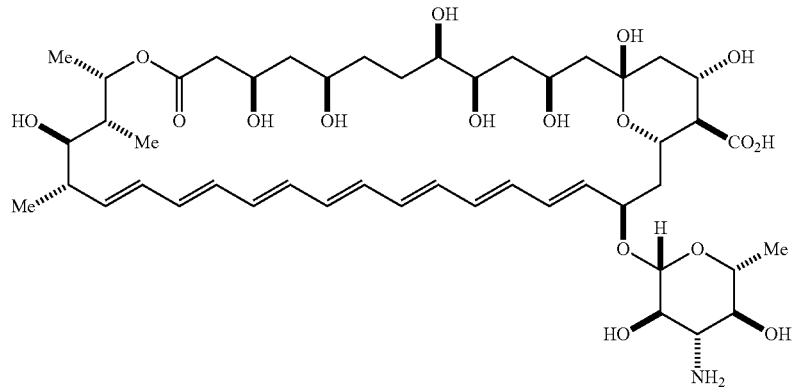

or a pharmaceutically acceptable salt thereof.

An aspect of the invention is a method of treating a yeast or fungal infection, comprising administering to a subject in need thereof a therapeutically effective amount of C2'epiAmB, represented by

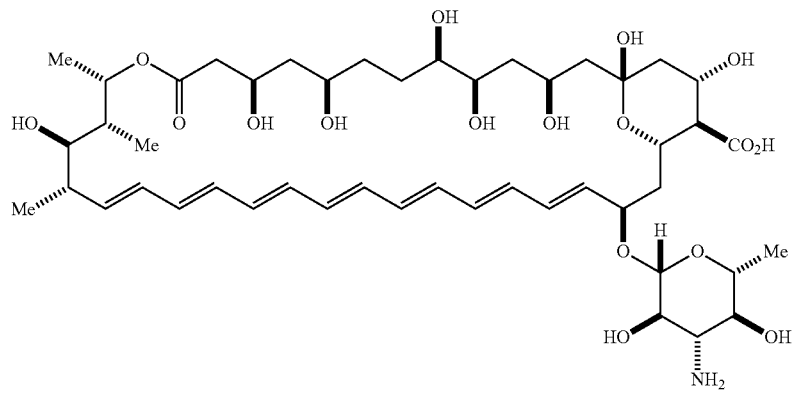

or a pharmaceutically acceptable salt thereof.

BRIEF DESCRIPTION OF THE DRAWINGS

FIG. 5 is a chart expressing binding affinity, anti-fungal activity, and toxicity data for C2'epiAmB. Chol, cholesterol; Erg, ergosterol; ITC, isothermal titration calorimetry; MHC, minimum hemolytic concentration; MIC, minimum inhibitory concentration; MTC, minimum toxic concentration; RBC, human red blood cells; REC, human renal epithelial cells.

DETAILED DESCRIPTION OF THE INVENTION

Amphotericin B (AmB) is a polyene macrolide with a mycosamine appendage, the complete compound having the following structure:

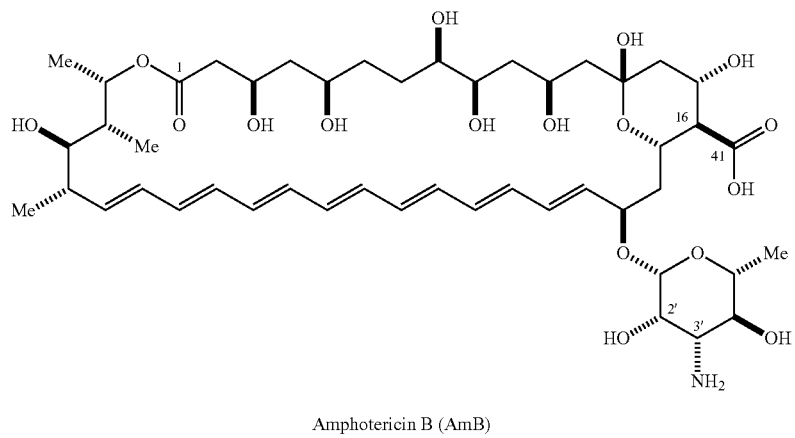

Amphotericin B (AmB)

Amphotericin B (AmB) is a clinically vital antimycotic but its use is limited by its toxicity. Binding ergosterol, independent of channel formation, is the primary mechanism by which AmB kills yeast, and binding cholesterol may primarily account for toxicity to human cells. A leading structural model predicts that the CT hydroxyl group on the mycosamine appendage is key to binding to both sterols.

AmB is generally obtained from a strain of *Streptomyces nodosus*. It is currently approved for clinical use in the United States for the treatment of progressive, potentially life-threatening fungal infections, including infections such as systemic candidiasis, aspergillosis, cryptococcosis, blastomycosis, coccidioidomycosis, histoplasmosis, and mucormycosis. AmB is generally formulated for intravenous injection. Amphotericin B is commercially available, for example, as Fungizone® (Squibb), Amphocin® (Pfizer), Abelcet® (Enzon), and Ambisome® (Astellas). Due to its unwanted toxic side effects, dosing is generally limited to a maximum of about 1.0 mg/kg/day, and total cumulative doses not to exceed about 3 g in humans.

It has for many decades been widely accepted that AmB primarily kills both yeast and human cells via membrane permeabilization.[7] Guided by this model, extensive efforts have focused on the development of derivatives that selectively form ion channels in yeast vs. human cells.[7b-e]

Figure 1A:
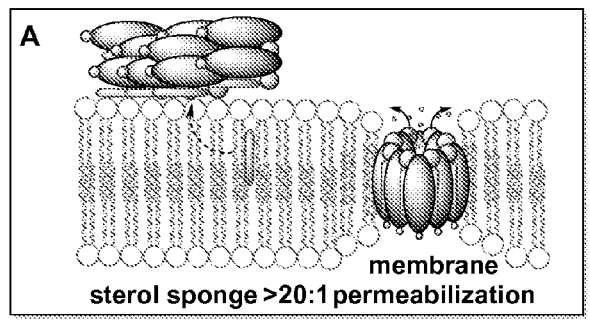
FIG. 1A depicts the activity of AmB as a sterol sponge. The discs that are depicted represent ergosterol.
Figure 1B:
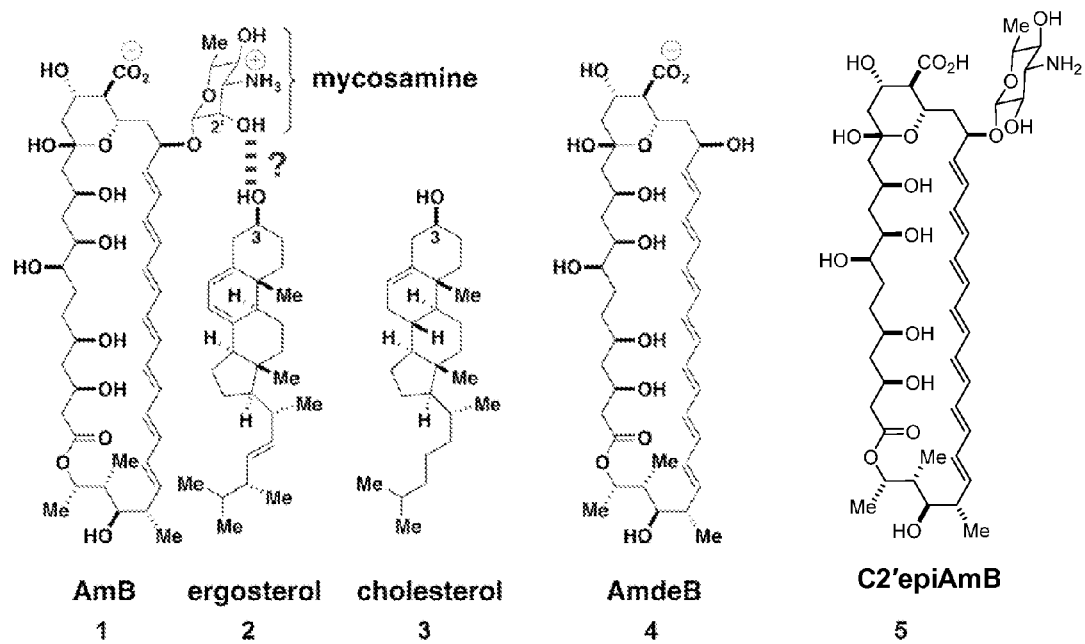
FIG. 1B depicts structures of amphotericin B (AmB, (1)) and synthetic derivatives AmdeB (4) and C2'epiAmB (5) thereof. Also depicted are structures of mycosamine, ergosterol (2), and cholesterol (3).
Figure 1C:
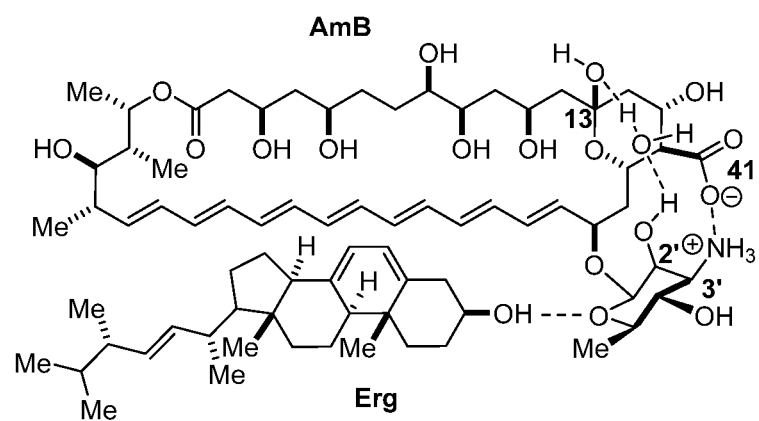
FIG. 1C is a drawing showing the two putative contact points between AmB and ergosterol (Erg).

In contrast to this classic model, it has been recently discovered that AmB self assembles into an extramembranous 'sterol-sponge'[8d] (FIG. 1A) that primarily kills cells by binding and extracting sterols in a mycosamine-dependent fashion.[8] Evidence supports a model in which the C2'-OH and C3'-$NH_3^+$ on the mycosamine appendage[9] are involved in stabilizing a ground state conformation of AmB that allows for the binding of both ergosterol (Erg) and cholesterol (Chol); i.e., channel formation is not required.[8] When either the C2'-OH or C3'-$NH_3^+$ is deleted, AmB still binds Erg but no longer binds Chol[9]. These results suggest the C2'-OH and the C3'-$NH_3^+$ do not directly bind sterols but are potential sites of allosteric modification (FIG. 1C). Furthermore, this shift in sterol binding directly correlates with a substantial decrease of observed toxicity to human cells[9]. This suggests that simply binding cholesterol may alternatively account for the toxicity of AmB to human cells, and that efforts to improve the therapeutic index of this clinically vital antimycotic can focus on the much simpler problem of maximizing the relative binding affinity for ergosterol vs. cholesterol.

Previously, it was found that deletion of the mycosamine appendage from AmB eliminates its capacity to bind both ergosterol and cholesterol.[8] The resulting derivative, amphoteronolide B (AmdeB), was also found to be non-toxic to yeast.[8] The roles played by each heteroatom contained in the mycosamine appendage, however, have remained unclear.

In the leading existing structural model, AmB binds both ergosterol and cholesterol via a similar complex in which the CT hydroxyl group of AmB forms a critical hydrogen bond to the 3-β hydroxyl group on each sterol (FIG. 1B).[10] However, strong evidence for or against this hypothesis was lacking For example, computer simulations[11] have suggested that such a hydrogen bond plays an important role in binding ergosterol, but not cholesterol. Alternatively, previous studies comparing the membrane permeabilizing activities of conformationally restricted derivatives of AmB[10c] concluded that such a hydrogen bond plays a key role with both sterols. None of these prior studies directly measured sterol binding.

Figure 2A:
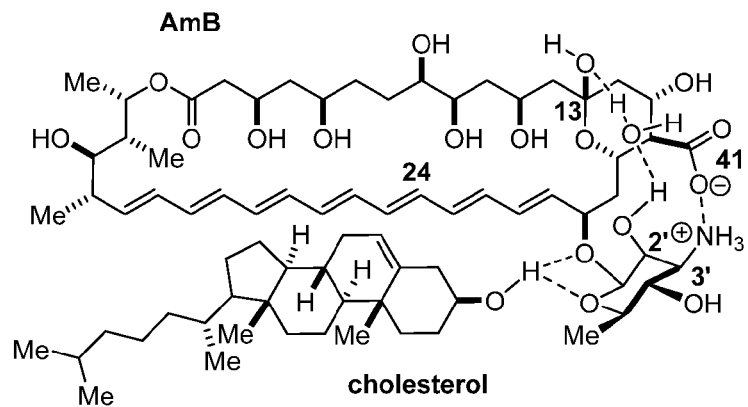
FIG. 2A depicts a representation of the N-iodoacylAmB crystal structure with cholesterol bound to the ground state conformation stabilized by two polar intramolecular contacts.
Figure 2B:
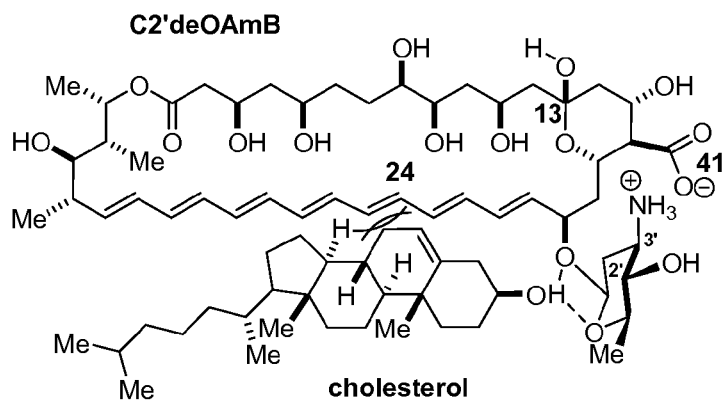
FIG. 2B depicts the inability of C2'deOAmB to bind cholesterol.

The relative exotherms observed in isothermal titration calorimetry (ITC) assays, and minimum inhibitory concentration (MIC) vs. minimum hemolytic concentration (MHC), suggest that AmB preferentially binds Erg over Chol. It is suggested that this predisposition is due to Chol being slightly bulkier than Erg. Furthermore, when allosteric modifications are made to AmB (i.e., deletion of either the C2'-OH or the C3'-$NH_3^+$), the natural sterol selectivity is magnified to favor only Erg binding (FIG. 2B). With these two potential sites of allostery identified, we proceeded to investigate how subtle modifications to the C2'-position might further magnify selectivity for binding Erg.

Figure 2C:
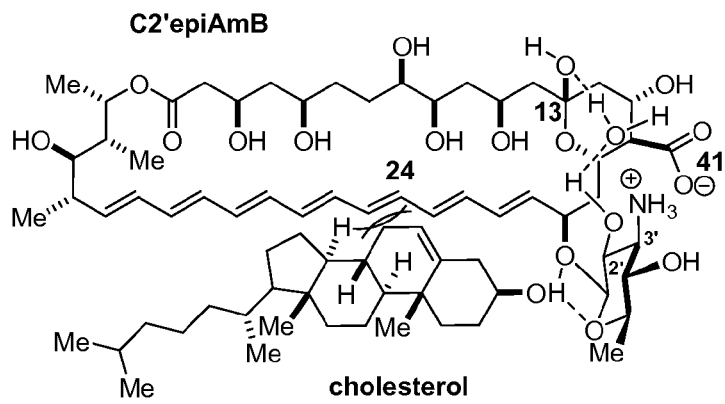
FIG. 2C depicts the inability of C2'epiAmB to bind cholesterol.

We hypothesized that epimerization of the C2'-OH would lead to a similar magnification of Erg binding as observed when the C2'-OH is deleted. Based on our understanding of a possible ground-state conformation of AmB (FIG. 2A)—informed by the N-IodoacylAmB crystal structure[8]—we proposed that a potential hydrogen bonding interaction between the C2'-OH, a molecule of water, and the C13-OH is implicated in AmB's ability to bind both Erg and Chol. Thus, epimerization at the C2'-position would potentially cause a disruption or alteration of this putative 'water bridge,' possibly leading to a change in shape of the sterol binding pocket that would result in an increased preference for Erg binding (FIG. 2C).

Figure 2D:
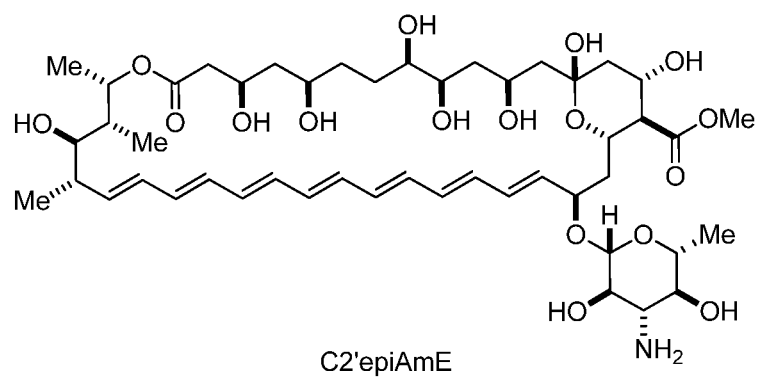
FIG. 2D depicts prior art compound C2'epiAmE.

The synthesis of doubly modified C2'epiAmB methyl ester (C2'epiAmE; FIG. 2D) was previously reported by Carreira and coworkers in 2011[9]. Interestingly, they observed that C2'epiAmE was equipotent to AmB in their yeast MIC assays. They also observed that it caused efflux of potassium ions from both Erg- and Chol-containing POPC liposomes at 1 μM. From these data, Carreira and coworkers concluded that "the configuration of C2'-position was inconsequential"[9]. Carreira and coworkers did not assay C2'epiAmE for human toxicity or Chol binding.

In accordance with the invention, the CT hydroxyl group was epimerized, as compared to AmB, and the impact of this modification on binding ergosterol and cholesterol was determined. Many of the experimental results are presented in the Exemplification section and the Figures. Remarkably, we have discovered a new efficacious non-toxic AmB derivative, C2'epiAmB, that has thus far shown the most potential as a clinically viable therapeutic replacement for AmB. Compared to AmB, C2'epiAmB retains the zwitterionic character of AmB, and differs only in the inversion of a single stereocenter.

With these remarkable in vitro results in hand, we also tested the efficacy and toxicity of C2'epiAmB in a mouse study in direct comparison to AmB and C2'deOAmB. The in vivo studies show C2'epiAmB to be equipotent to AmB yet substantially less toxic to mice. Furthermore, since there is a hydroxyl group at the C2'-position, we predict that C2'epiAmB should be as stable as AmB in vivo.

An aspect of the invention is C2'epiAmB, represented by

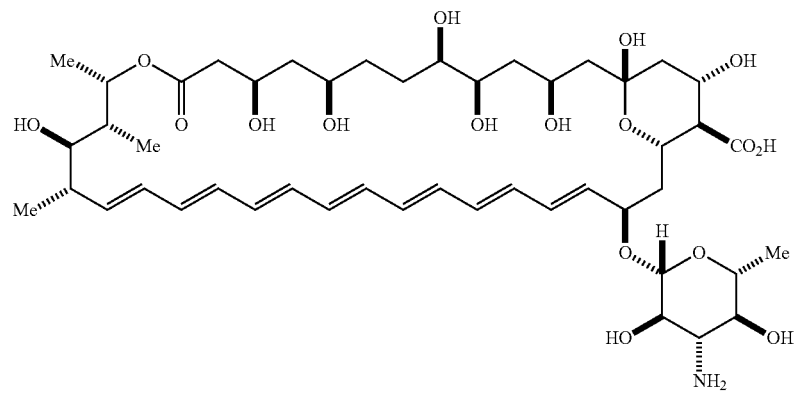

or a pharmaceutically acceptable salt thereof. Methods for making C2'epiAmB are disclosed herein below.

A "compound of the invention" as used herein refers to C2'epiAmB and any of the foregoing pharmaceutically acceptable salts thereof.

An aspect of the invention is a pharmaceutical composition, comprising C2'epiAmB, represented by

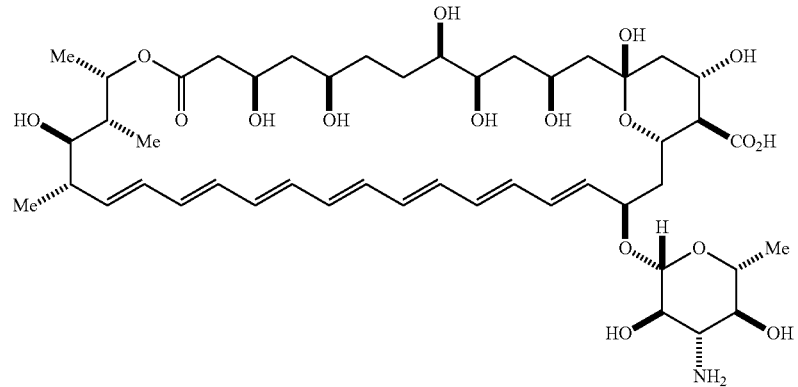

or a pharmaceutically acceptable salt thereof; and a pharmaceutically acceptable carrier. As described in further detail below, the term "pharmaceutically acceptable carrier" means one or more compatible solid or liquid filler, diluent, or encapsulating substances which are suitable for administration to a human or other subject.

An aspect of the invention is a method of inhibiting growth of a yeast or fungus, comprising contacting the yeast or fungus with an effective amount of C2'epiAmB, represented by

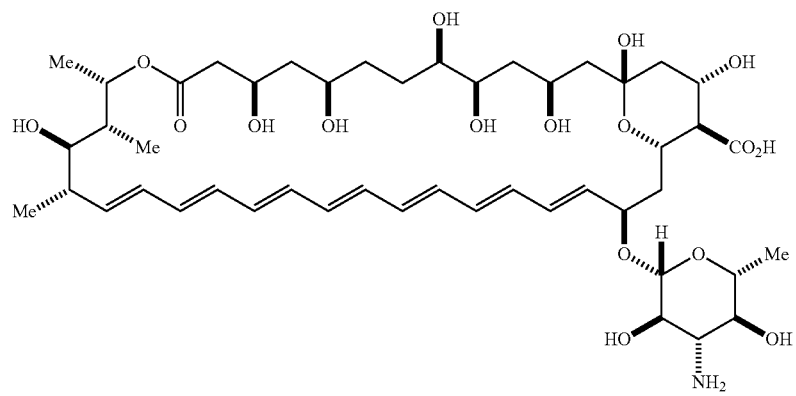

or a pharmaceutically acceptable salt thereof.

Yeasts are eukaryotic organisms classified in the kingdom Fungi. Yeasts are typically described as budding forms of fungi. Of particular importance in connection with the invention are species of yeast that can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic yeasts include, without limitation, various species of the genus *Candida*, as well as of *Cryptococcus*. Of particular note among pathogenic yeasts of the genus *Candida* are *C. albicans, C. tropicalis, C. stellatoidea, C. glabrata, C. krusei, C. parapsilosis, C. guilliermondii, C. viswanathii*, and *C. lusitaniae*. The genus *Cryptococcus* specifically includes *Cryptococcus neoformans*. Yeast can cause infections of mucosal membranes, for example oral, esophageal, and vaginal infections in humans, as well as infections of bone, blood, urogenital tract, and central nervous system. This list is exemplary and is not limiting in any way.

Fungi include, in addition to yeasts, other eukaryotic organisms including molds and mushrooms. A number of fungi (apart from yeast) can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic fungi (apart from yeast) include, without limitation, species of *Aspergillus, Rhizopus, Mucor, Histoplasma, Coccidioides, Blastomyces, Trichophyton, Microsporum*, and *Epidermophyton*. Of particular note among the foregoing are *A. fumigatus, A. flavus, A. niger, H. capsulatum, C. immitis*, and *B. dermatitidis*. Fungi can cause deep tissue infections in lung, bone, blood, urogenital tract, central nervous system, to name a few. Some fungi are responsible for infections of the skin and nails.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent compared to control.

An aspect of the invention is a method of treating a yeast or fungal infection, comprising administering to a subject in need thereof a therapeutically effective amount of C2'epiAmB, represented by

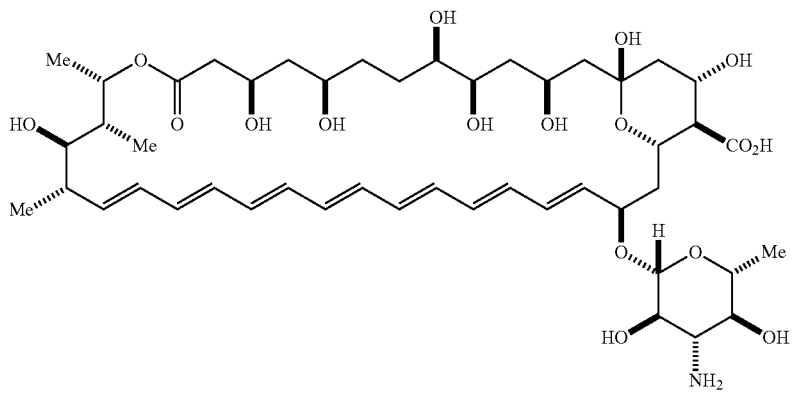

or a pharmaceutically acceptable salt thereof.

As used herein, the terms "treating" and "treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

A "yeast infection" as used herein refers to an infection with a yeast as defined herein.

A "fungal infection" as used herein refers to an infection with a fungus as defined herein.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a yeast or fungal infection" refers to a subject that exhibits at least one objective manifestation of a yeast or fungal infection. In one embodiment a subject having a yeast or fungal infection is a subject that has been diagnosed as having a yeast or fungal infection and is in need of treatment thereof. Methods of diagnosing a yeast or fungal infection are well known and need not be described here in any detail.

As used herein, "administering" has its usual meaning and encompasses administering by any suitable route of administration, including, without limitation, intravenous, intramuscular, intraperitoneal, subcutaneous, direct injection (for example, into a tumor), mucosal, inhalation, oral, and topical.

In one embodiment, the administration is systemically administering.

In one embodiment, the administration is topically administering.

As used herein, the phrase "effective amount" refers to any amount that is sufficient to achieve a desired biological effect. As used herein, the phrase "therapeutically effective amount" refers to any amount that is sufficient to achieve a desired therapeutic effect, e.g., to treat a yeast or fungal infection.

Compounds and salts of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include other antifungal agents, including AmB, as well as other antibiotics, anti-viral agents, anti-inflammatory agents, immunosuppressive agents, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily intravenous doses of C2'epiAmB will be, for human subjects, similar to or greater than usual daily intravenous doses of AmB. Similarly, daily other parenteral doses of C2'epiAmB will be, for human subjects, similar to or greater than usual daily parenteral doses of AmB.

In one embodiment, intravenous administration of a compound of the invention may typically be from 0.1 mg/kg/day to 20 mg/kg/day. In one embodiment, intravenous administration of a compound of the invention may typically be from 0.1 mg/kg/day to 2 mg/kg/day. In one embodiment, intravenous administration of a compound of the invention may typically be from 0.5 mg/kg/day to 5 mg/kg/day. In one embodiment, intravenous administration of a compound of the invention may typically be from 1 mg/kg/day to 20 mg/kg/day. In one embodiment, intravenous administration of a compound of the invention may typically be from 1 mg/kg/day to 10 mg/kg/day. Intravenous dosing thus may be similar to, or advantageously, may exceed maximal tolerated doses of AmB.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, C2'epiAmB generally may be formulated similarly to AmB. For example, C2'epiAmB can be formulated as a lyophilized preparation with desoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., C2'epiAmB and pharmaceutically acceptable salts thereof, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents can be used and can include, for example, benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, C2'epiAmB for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of C2'epiAmB (or salts thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of C2'epiAmB (or salt thereof). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or salt thereof) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers ($\mu$m), most preferably 0.5 to 5 $\mu$m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, C2'epiAmB may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990).

C2'epiAmB and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of C2'epiAmB and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to C2'epiAmB, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, non-erodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

General Methods

Materials

Commercially available materials were purchased from Sigma-Aldrich, Alfa Aesar, Strem, or Fisher Scientific, and were used without further purification unless stated otherwise. Amphotericin B was a generous gift from Bristol-Myers Squibb Company. Camphorsulfonic acid was recrystallized from the ethyl acetate prior to use. All solvents were dispensed from a solvent purification system that purifies solvents by passage through packed columns according to the method of Pangborn and coworkers (THF, $Et_2O$, $CH_2Cl_2$, $CH_3N$, dioxane, hexanes: dry neutral alumina; benzene, toluene: dry neutral alumina and Q5 reactant; DMSO, DMF, $CH_3OH$: activated molecular sieves). Ermishkin, L N et al. (1976) *Nature* 262:698-699. Water was doubly distilled or obtained from a Millipore (Billerica, Mass.) MilliQ water purification system. Triethylamine was freshly distilled under an atmosphere of nitrogen from CaH$_2$. (±)-10-Camphorsulfonic acid was recrystallized from EtOAc.

Reactions

Due to the light and air sensitivity of polyenes, all manipulations of polyenes were carried out under low light conditions and compounds were stored under an argon atmosphere. All reactions were performed in oven-dried (~125° C.) or flame-dried glassware under an atmosphere of argon unless otherwise indicated. Reactions were monitored by analytical thin layer chromatography performed using the indicated solvent on E. Merck silica gel 60 F$_{254}$ plates (0.25 mm). Compounds were visualized using a UV ($\lambda_{254}$) lamp or stained by a solution of p-anisaldehyde stain, followed by heating with a Varitemp heat gun. Flash column chromatography was performed using Merck silica gel 60 (230-400 mesh).

Purification and Analysis $^1$H NMR spectra were recorded at ambient temperature using one of the following instruments: Varian Unity 500 (500 MHz), Varian VXR 500 (500 MHz), or Varian Unity Inova 500NB (500 MHz). Chemical shifts are reported in parts per million (ppm) downfield from tetramethylsilane and referenced to residual protium in the NMR solvent (CDCl$_3$, δ=7.26; (CD$_3$)$_2$CO, δ=2.05, center line). Spectral data are presented as follows: chemical shift, multiplicity (s=singlet, d=doublet, t=triplet, q=quartet, sext=sextet, dd=doublet of doublets, dt=doublet of triplets, ddd=doublet of doublet of doublets, m=multiplet, b=broad, app=apparent), coupling constant (J), and integration. $^{13}$C NMR spectra were recorded at ambient temperature using one of the following instruments: Varian VXR 500 (125 MHz), Varian Unity 500 (125 MHz), or Varian Unity 400 (101 MHz) instrument. Chemical shifts are reported in ppm downfield from tetramethylsilane and referenced to carbon resonances in the NMR solvent (CDCl$_3$, δ=77.16, center line; CD$_3$C(O)CD$_3$, δ=29.84, center line). High-resolution mass spectra (HRMS) were acquired by Mr. Pulin Wang, Mr. Furong Sun, or Dr. Haijun Yao at the University of Illinois School of Chemical Sciences Mass Spectrometry Laboratory. Data are reported in the form of m/z. Gas chromatography analysis was conducted on an Agilent Technologies 7890A instrument.

Extinction Coefficient Determination

A sample of dried compound was massed in a tared vial using a Mettler Toledo MT5 microbalance. This sample was then dissolved in DMSO to create a concentrated stock solution. A portion of this concentrated stock solution was diluted by a factor of five with DMSO to create a dilute stock solution. To achieve the final concentration for UV/Vis experiments, a volume of the dilute stock solution was diluted to 0.5 mL with MeOH. For each compound, UV/vis experiments were performed using five different final concentrations, and each concentration was prepared three times to obtain an average absorbance. The average absorbance was plotted against the concentration. The data was fitted with a linear least squares fit using Excel, and the slope of the fitted line was used as the extinction coefficient. The extinction coefficients were as follows: AmB ($\epsilon_{406}$=164,000), AmdeB ($\epsilon_{406}$=102,000), C2'deOAmB ($\epsilon_{406}$=73,000).

Example 1

Synthesis of C2'epiAmB

In the first generation synthesis of C2'epiAmB, the Carreira synthesis of C2'epiAmE was modified to allow access to the deprotected material. Specifically, a readily removable allyl ester was employed at the C41-position. Employing a previously reported route to the fully protected aglycone 5.5[3b,5] with the mycosamine donor and glycosylation conditions previously used in the construction of C3'deNHAmB[5], C2'epiAmB was synthesized (FIG. 3).

Figure 4:
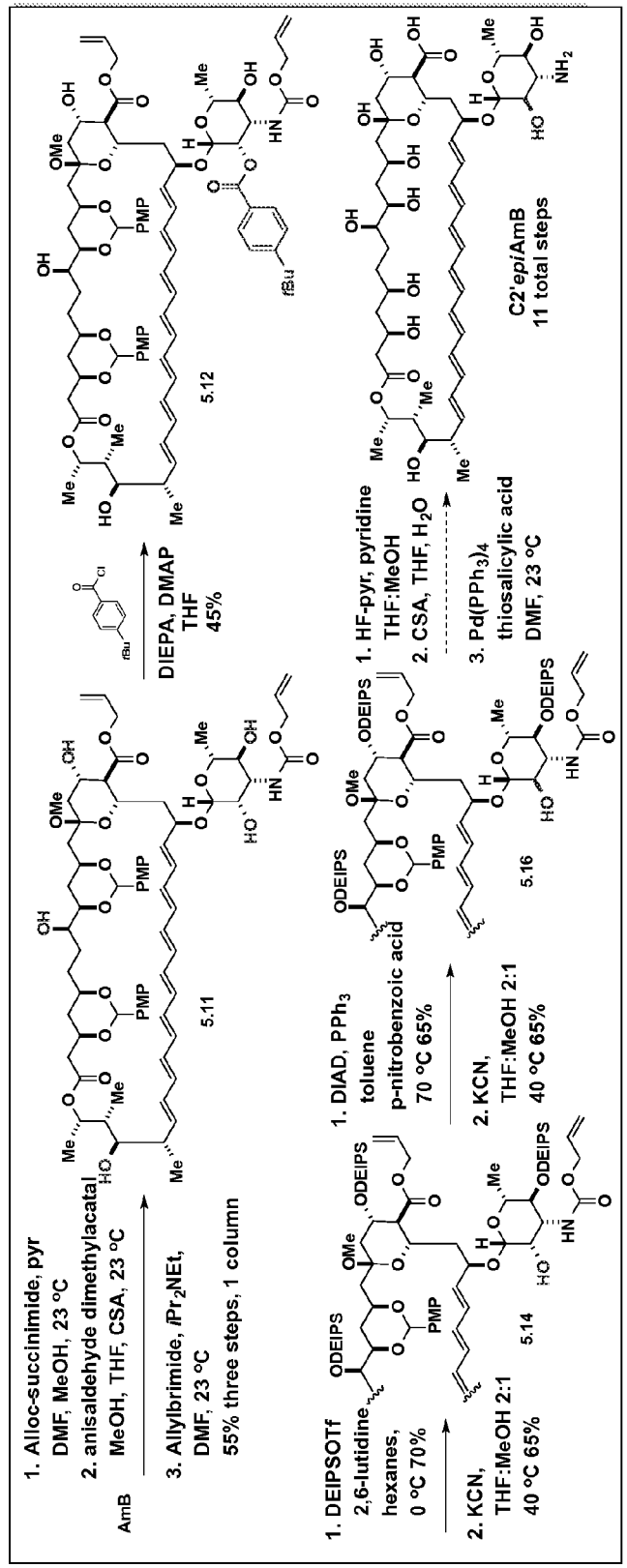
FIG. 4 depicts a scheme for synthesis of C2'epiAmB.

Although the synthesis of C2'epiAmB was possible from a hybrid glycosylation route similar to C2'deOAmB[4] and C3'deNHAmB[5], we realized that our previously reported site-selective acylation methodology of AmB could provide a more efficient and practical synthesis of C2' epiAmB In the second-generation synthesis of C2'epiAmB, depicted in FIG. 4, a different protecting group strategy was employed. Alloc was installed as the protecting group on the nitrogen. The C41 carboxylate was protected with an allyl group. Both of these groups would be concomitantly removed in the final step with Pd(PPh$_3$)$_4$ and thiosaliscylic acid. The PMP ketals were critical for the selective acylation methodology and could be simultaneously removed with the C13 methylketal as the penultimate step under mild acidic conditions. Diethylisopropyl silyl (DEIPS) ether groups were used because they are robust enough to survive the KCN mediated hydrolysis of both C2'benzoate intermediates, yet easily removed with pyridine buffered HF-pyridine conditions[11].

In the forward sense, the Alloc group, hemiketal, PMP ketals, and allyl groups were installed in three steps from AmB with one chromatographic separation affording 5.11 in 55% yield. At this point the C2'-OH of 5.11 was selectively acylated with p-tertbutylbenzoyl chloride under the previously reported conditions to generated 4.12 in a preoperatively useful 30% yield. DEIPS groups were installed using the corresponding triflate, affording 5.13 in 72% yield. Subsequent KCN mediated hydrolysis of the C2' p-tertbutylbenzoate provided free C2'-OH 5.14 in 63% yield. Inverting the C2'-OH of 5.14 proceeded under Mitsunobu conditions affording C2' equatorial p-nitrobenzoate 5.15 in 65% yield. The resulting C2'-nitrobenzoate 5.15 was the cleaved with similar KCN conditions to generate fully protected C2'epiAmB 5.16. Three global deprotection steps remain in the 2$^{nd}$ generation route to C2'epiAmB: 1) HF-pyridine desilylation; 2) ketal hydrolysis with trifluoroacetic acid in DMF; and 3) concomitant removal of the allyl ester and alloc groups with Pd(PPh$_3$)$_4$ and thiosalicylic acid.

Figure 3:
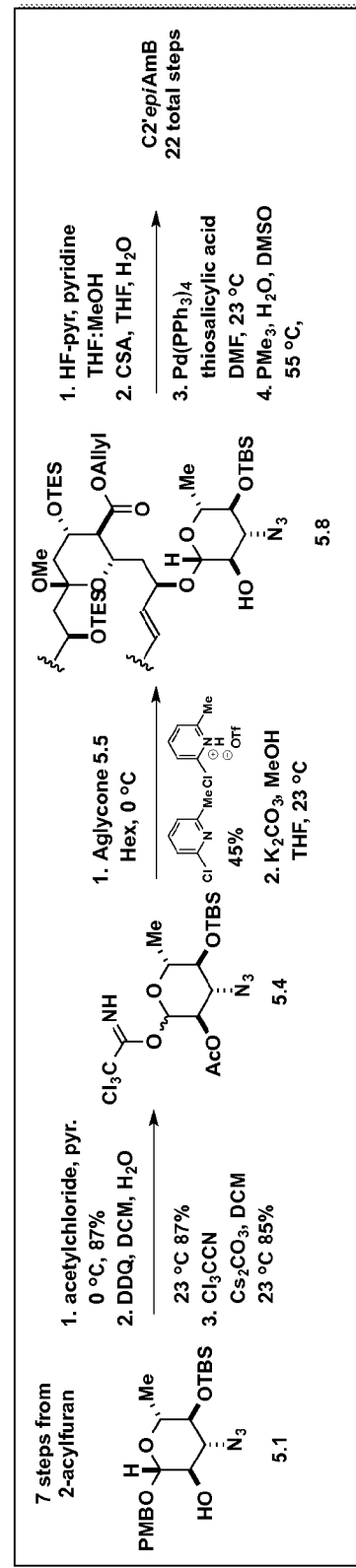
FIG. 3 depicts a scheme for synthesis of C2'epiAmB.

Details of the synthesis depicted in FIG. 3 and FIG. 4 are as follows.

Synthesis of Intermediate 5.2

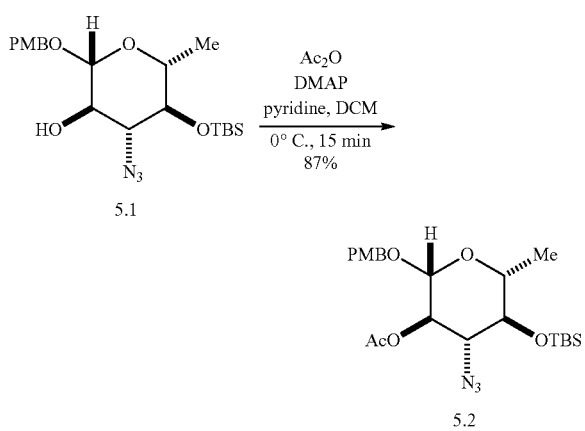

To a stirred solution of azido alcohol 5.1 (1.14 g, 2.69 mmol, 1.0 equiv.) and pyridine (2.17 mL, 26.87 mmol, 10.0 equiv.) in 27 mL DCM at 0° C. in a 100 mL round bottom flask were sequentially added acetic anhydride (1.27 mL, 13.4 mmol, 5.0 equiv.) and DMAP (16.4 mg, 0.135 mmol, 0.05 equiv). After 15 min the solution was warmed to 23° C., stirred for 10 min, poured into a reparatory funnel containing Et₂O and saturated aqueous bicarbonate. The aqueous layer was extracted with Et₂O (3×20 mL) and the combined organic layers were dried over sodium sulfate, filtered and concentrated under reduced pressure. The pyridine was removed azeotropically with benzene (3×15 mL). Purified by flash chromatography (gradient elution, 5% EtOAc:Hex to 10% EtOAc:Hex) afforded acetate 5.2 (1.09 g, 2.34 mmol, 87%) as a clear, colorless oil.

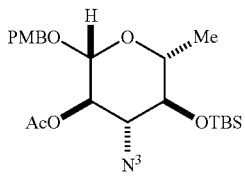

5.2

$R_f$=0.65 (1:1 Et₂O/Hex, CAM stain)
¹H NMR: (500 MHz, CD₃C(O)CD₃) δ 7.33-7.28 (m, 2H), 6.95-6.90 (m, 2H), 4.97 (d, J=3.7 Hz, 1H), 4.68 (d, J=11.8 Hz, 1H), 4.64 (dd, J=10.6, 3.7 Hz, 1H), 4.47 (d, J=11.7 Hz, 1H), 3.80 (s, 3H), 3.77-3.72 (m, 2H), 3.23 (t, J=9.2 Hz, 1H), 2.09 (s, 1H), 2.07 (s, 3H), 1.24 (d, J=6.2 Hz, 3H), 0.93 (s, 11H).
HRMS (ESI)
Calculated for C₂₂H₃₅N₃O₆Si (M+Na)+: 488.2193.
Found: 488.2193.

Synthesis of Intermediate 5.3

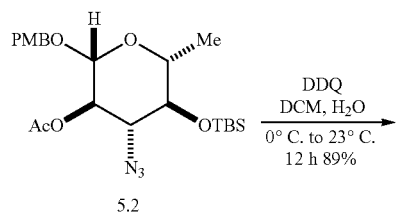

To a stirred solution of acetate 5.2 (1.09 g, 2.34 mmol, 1.0 equiv.) in a mixture of DCM:H₂O (23.4 mL, 10:1) at 0° C. in a foil-covered 40 mL iChem vial was added DDQ (623 mg, 2.81 mmol, 1.2 equiv). After 5 min, the reaction was warmed to 23° C., stirred for 12 h, and poured into a separatory funnel containing Et₂O and saturated aqueous bicarbonate. Organics were washed with saturated brine. The combined aqueous layers were extracted with Et₂O (3×20 mL) and the combined organic layers were dried over sodium sulfate, filtered and concentrated under reduced pressure. Purification by flash chromatography (SiO₂, gradient elution, 10% EtoAc:Hex to 15% EtoAc:Hex to 20% EtoAc:Hex) afforded hemiketal 5.3 (716 mg, 2.07 mmol, 89%) as a clear, colorless oil.

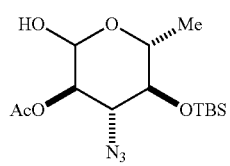

5.3

$R_f$=0.45 (1:1 Et₂O/Hex, CAM stain)
¹H NMR: ¹H NMR (500 MHz, CD₃C(O)CD₃) δ 5.23 (d, J=3.7 Hz, 1H), 4.61 (dd, J=10.5, 3.6 Hz, 1H), 3.92 (dq, J=9.2, 6.3 Hz, 1H), 3.77 (dd, J=10.5, 9.2 Hz, 1H), 3.19 (t, J=9.2 Hz, 1H), 2.09 (s, 3H), 2.08 (d, J=1.7 Hz, 1H), 1.24 (d, J=6.2 Hz, OH), 1.19 (d, J=6.3 Hz, 4H), 0.94 (s, 10H), 0.93 (s, 2H), 0.21 (d, J=3.3 Hz, 4H), 0.15 (s, 4H).
HRMS (ESI)
Calculated for C₁₄H₂₇N₃O₅Si (M+Na)⁺: 368.1618.
Found: 368.1620.

Synthesis of Intermediate 5.4

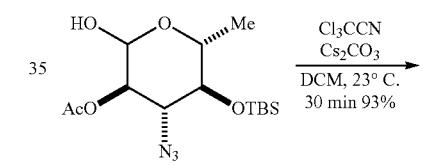

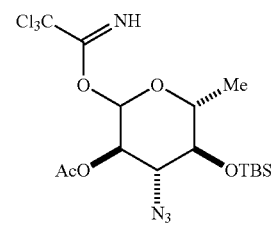

5.4

To a stirred solution of hemiketal 5.3 (716 mg, 2.07 mmol, 1.0 equiv.) in 10.35 mL DCM, at 23° C. in a 40 mL iChem vial were sequentially added trichloroacetonitrile (1.04 mL, 10.35 mmol, 5.0 equiv.) and cesium carbonate (337.2 mg, 1.03 mmol, 0.5 equiv.). After 30 min, the reaction was poured into a separatory funnel containing hexanes and water. The layers were separated, the aqueous phase was extracted with hexane (3×30 mL) and the combined organic layers were dried over sodium sulfate, filtered and concentrated under reduced pressure. Exogenous water was azeotropically removed with benzene (3×10 mL) and trichloroacetimidate 5.4 was used without further purification in the subsequent reaction. Since this product was not stable, it was either used immediately after formation or frozen in a benzene argon matrix.

5.4

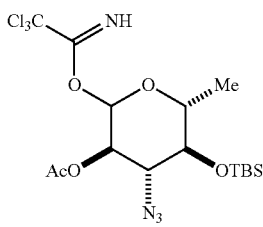

$R_f$=0.95 (1:1 Et$_2$O/Hex with 0.1% Et$_3$N CAM stain)

Synthesis of Intermediate 5.6 vac overnight in a 500 mL round bottom flask. Trichloroacetimidate 5.4 (944 mg, 1.93 mmol, 1.44 equiv.) was added to the flask containing 5.5 as a solution in benzene and concentrated down. Hexanes (70 mL) was added and subsequently cooled to 0° C. after the system was placed under an N$_2$ atmosphere. 2-chloro-6-methylpyridine (147 mL, 1.34 mmol, 1.0 equiv.) was added followed by 2-chloro-6-methylpyridinium triflate (186.0 mg, 0.67 mmol, 0.5 equiv.) as a solid in one portion. After 8 min a color change was observed from orange to greenish yellow and slight precipitate formation. The reaction was quenched at 30 min after addition of triflate salt by pouring into a reparatory funnel containing hexanes and saturated aqueous sodium bicarbonate. The aqueous phase was extracted with hexanes (2×50 mL) and the subsequent organic phases were washed with

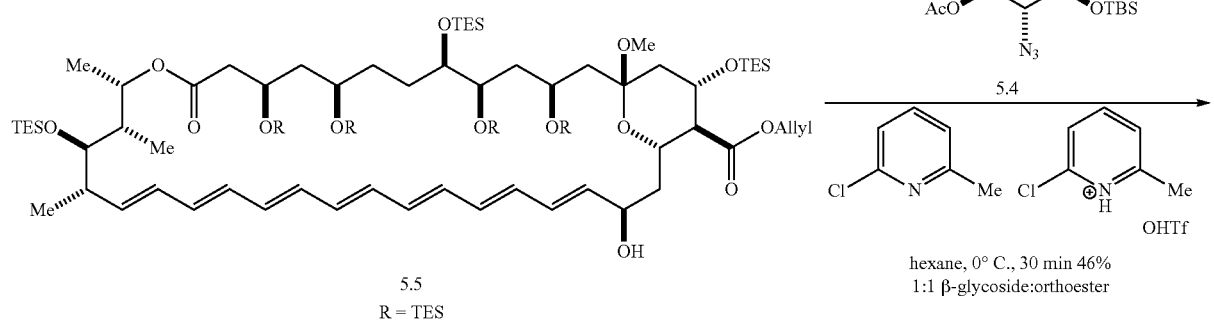

5.5
R = TES hexane, 0° C., 30 min 46%
1:1 β-glycoside:orthoester

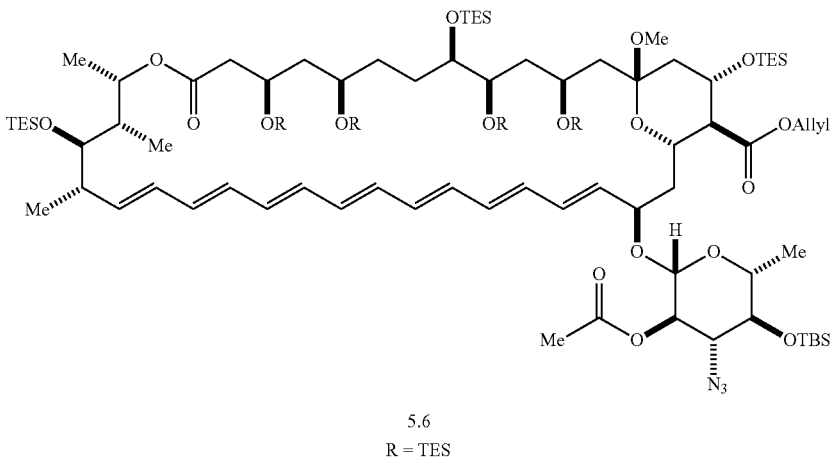

5.6
R = TES

AmB aglycone 5.5 (2.19 g, 1.34 mmol, 1.0 equiv.) was azeotripically dried with benzene (3×10 mL) and left on high saturated brine then dried over sodium sulfate, filtered and concentrated under reduced pressure. Purification by flash chromatography (gradient elution 5:95 EtOAc:Hex to 1:9 EtOAc:Hex) afforded an inseparable 1:1 mixture of β-glycoside 5.6 and its orthoester (1.21 g, 46% yield) as a yellowish-orange solid. This mixture was carried on to the subsequent reaction where cleavage of the acetate group provides an isolable product.

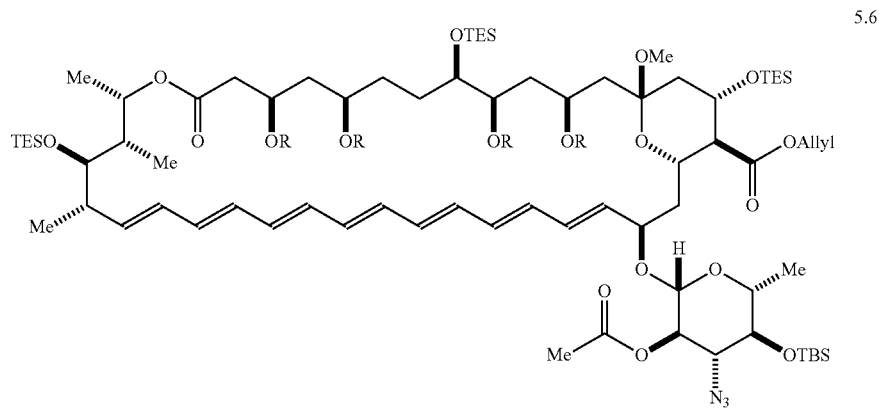

5.6
R = TES $R_f$=0.73 (1:9 EtOAc:Hex, CAM stain)
$^1$H NMR: (500 MHz, CD$_3$C(O)CD$_3$) δ 6.52 (ddd, J=14.0, 10.5, 3.3 Hz, 5H), 6.46-5.97 (m, 31H), 5.53 (ddd, J=14.3, 9.5, 3.6 Hz, 2H), 4.76-4.54 (m, 11H), 4.45 (td, J=10.5, 4.7 Hz, 3H), 4.29-4.19 (m, 4H), 4.15 (s, 3H), 4.07-3.99 (m, 4H), 3.92-3.83 (m, 3H), 3.77-3.67 (m, 4H), 3.67-3.59 (m, 4H), 3.15 (s, 3H), 3.07 (s, 4H), 2.68-2.52 (m, 5H), 2.44 (q, J=8.3 Hz, 2H), 2.24 (s, 3H), 2.13-1.98 (m, 150H), 1.98-1.59 (m, 39H), 1.52 (d, J=12.6 Hz, 3H), 1.28 (d, J=9.1 Hz, 3H), 1.25 (d, J=6.2 Hz, 7H), 1.18 (d, J=6.0 Hz, 8H), 1.13-0.91 (m, 191H), 0.91-0.82 (m, 5H), 0.81-0.56 (m, 112H), 0.22 (d, J=1.2 Hz, 7H), 0.16 (d, J=3.4 Hz, 7H).
$^{13}$C NMR: (126 MHz, Acetone) δ 172.89, 139.33, 135.50, 134.89, 133.85, 133.69, 133.06, 132.81, 132.76, 131.64, 130.31, 129.83, 119.34, 119.04, 101.55, 98.52, 77.20, 76.93, 75.92, 74.28, 74.20, 72.97, 71.35, 70.50, 69.63, 69.27, 68.93, 67.71, 67.11, 66.27, 66.17, 58.17, 48.33, 48.26, 43.72, 41.49, 32.51, 30.51, 30.35, 30.20, 30.05, 29.89, 29.74, 29.66, 29.58, 27.74, 26.46, 26.38, 24.37, 21.12, 20.18, 19.53, 18.88, 18.81, 18.75, 18.73, 14.58, 11.33, 7.91, 7.88, 7.87, 7.75, 7.69, 7.56, 7.54, 7.48, 7.38, 7.37, 6.68, 6.65, 6.41, 6.13, 6.08, 6.04, 6.02, 5.96, 5.90, 5.86, 1.33, −3.83, −3.86, −4.01, −4.04.
HRMS (ESI)
Calculated for C$_{101}$H$_{191}$N$_3$O$_{18}$Si$_8$ (M+Na)$^+$: 1981.2175. Found: 1981.2169.

Synthesis of Intermediate 5.7

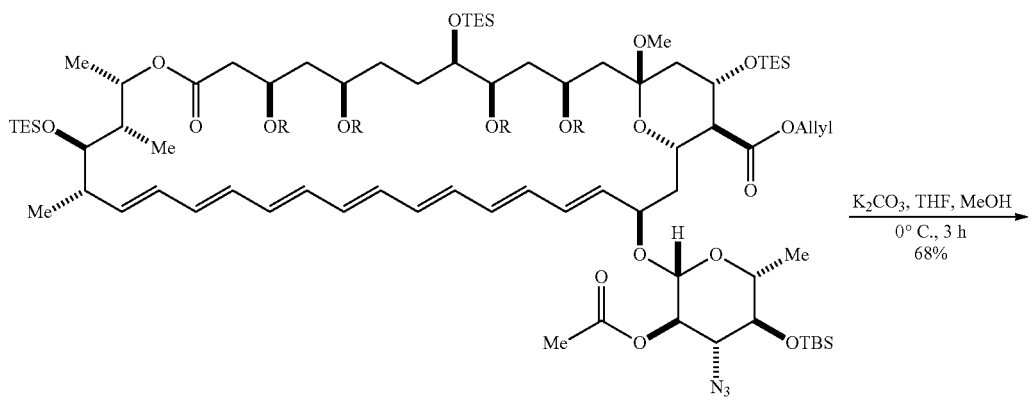

5.6
R = TES

-continued

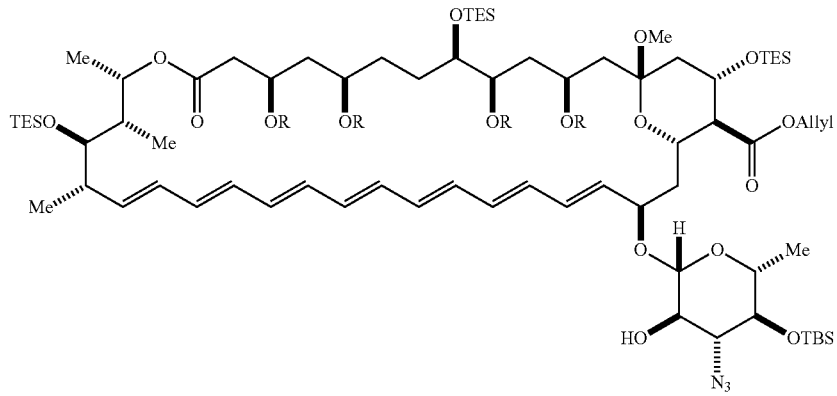

5.7
R = TES

To a stirred solution of a mixture of 5.6 and the corresponding orthoester as a 1:1 mixture (1.01 g, 0.515 mmol, 1.0 equiv.) in THF:MeOH (51 mL: 51 mL) at 0° C. in a 200 mL round bottom flask was added K$_2$OC$_3$ (2.85 g, 20.6 mmol, 40.0 equiv). After stirring at 0° C. for 2.5 hours the reaction was allowed to warm to 23° C. and stir for an additional 1.5 h. The reaction was then worked up by transferring to a reparatory funnel containing saturated brine and hexanes. The combined organic phases were washed with saturated aqueous bicarbonate, followed by DI water, saturated brine, and then they were dried over sodium sulfate, filtered and concentrated under reduced pressure. Purification by flash chromatography (gradient elution 5:95 EtOAc:Hex isocratic) afforded pure persilyl-C41allyl-C2'epiOH-methylketal-azidoAmB 5.7 (333 mg, 0.174 mmol, 68% based on 0.2575 mmol) as an orange-yellow solid.

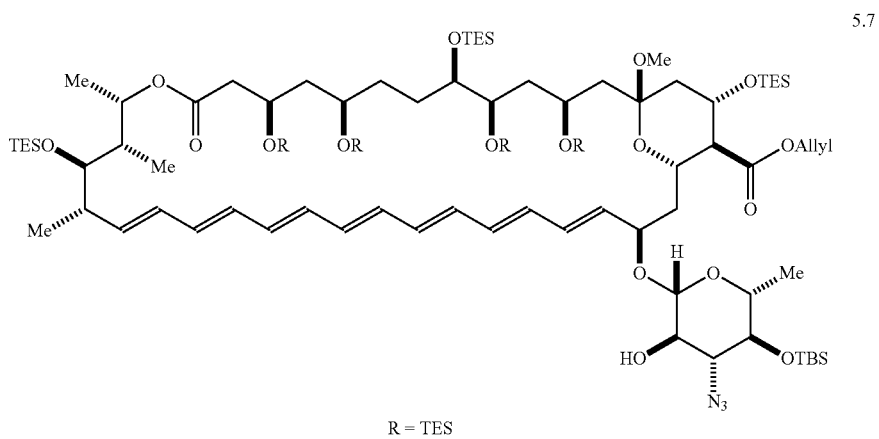

5.7
R = TES $R_f$=0.62 (1:9 EtOAc:Hex, CAM stain)
$^1$H NMR: (500 MHz, CD$_3$C(O)CD$_3$) δ 6.57-5.97 (m, 14H), 4.74-4.59 (m, 3H), 4.43 (q, J=6.2, 5.3 Hz, 1H), 4.38 (d, J=7.5 Hz, 1H), 4.21 (s, 1H), 4.05 (qd, J=8.1, 7.6, 4.8 Hz, 3H), 3.71 (dt, J=6.5, 4.5 Hz, 1H), 3.64 (dd, J=10.6, 4.7 Hz, 1H), 3.35 (ddt, J=10.3, 4.1, 2.6 Hz, 2H), 3.28 (t, J=9.4 Hz, 1H), 3.15 (s, 3H), 3.08 (t, J=9.0 Hz, 1H), 2.63-2.52 (m, 2H), 2.09 (s, 1H), 1.99-1.69 (m, 14H), 1.69-1.57 (m, 5H), 1.57-1.46 (m, 3H), 1.40-1.23 (m, 33H), 1.23-1.09 (m, 10H), 1.09-0.91 (m, 90H), 0.91-0.82 (m, 29H), 0.80-0.55 (m, 48H), 0.21 (s, 3H), 0.14 (s, 3H).

$^{13}$C NMR: (126 MHz, CD$_3$C(O)CD$_3$) δ 172.81, 169.91, 134.76, 134.17, 133.32, 132.81, 132.48, 132.00, 131.80, 131.69, 130.73, 130.06, 129.88, 118.41, 101.82, 100.77, 76.58, 76.07, 75.14, 73.90, 73.40, 72.96, 70.94, 70.47, 68.41, 66.87, 66.71, 65.53, 59.87, 56.85, 47.52, 43.65, 42.83, 40.70, 36.83, 36.21, 34.60, 31.66, 29.65, 28.73, 26.87, 25.66, 25.52, 25.15, 22.64, 20.26, 20.17, 19.31, 18.37, 18.10, 18.07, 13.85, 13.71, 11.04, 10.56, 7.03, 7.01, 6.89, 6.77, 6.70, 6.67, 6.53, 5.77, 5.71, 5.55, 5.29, 5.27, 5.24, 5.21, 5.17, 5.02, −4.53, −4.73.

HRMS (ESI)

Calculated for C$_{99}$H$_{189}$N$_3$O$_{17}$Si$_8$ (M+Na)$^+$: 1939.2069. Found: 1939.2126.

Synthesis of Intermediate 5.8

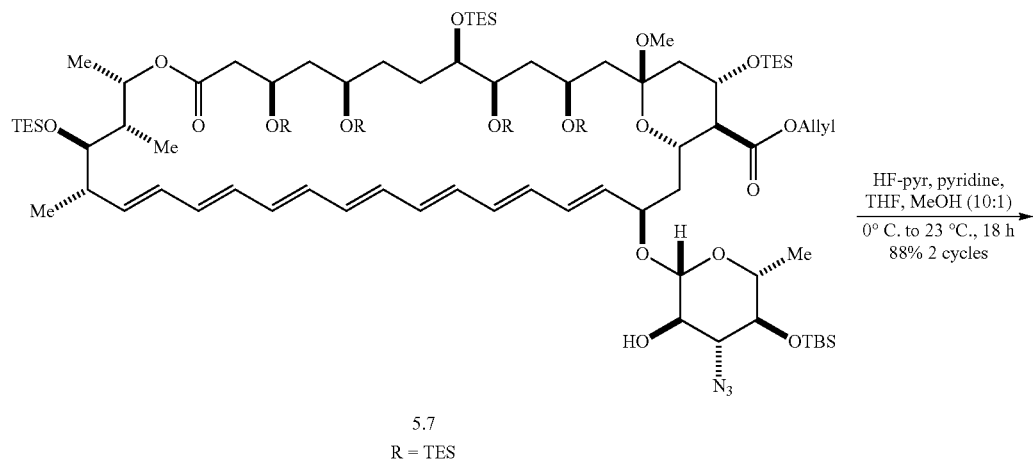

5.7
R = TES

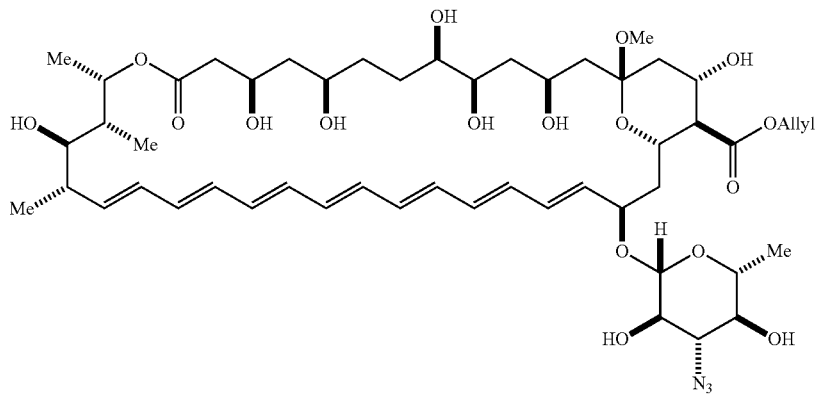

5.8

To a stirred solution of pyridine (5 mL, 62 mmol, 351 equiv.) in MeOH 250 μL in a 50 mL Teflon vial at 0° C. was added drop-wise HF-pyridine 70% complex (1.04 mL, 328 equiv.). To this solution was added via cannula 5.7 (333 mg, 174 μmol, 1.0 equiv.) as a solution in THF (1.5 mL). The vial containing 5.7 was washed with THF (3×500 μL) to ensure quantitative transfer of material. The reaction was then allowed to warm to 23° C. and stirred for 18 h. the reaction was then cooled to 0° C. and quenched via slow addition of MeOSiMe$_3$ (gross excess) then allowed to warm to 23° C. and stirred for 1 h. The reaction was then concentrated under reduced pressure and pyridine was azeotropically removed with benzene (3×15 mL). Purification by preparative reverse phase HPLC (C$_{18}$ SiO$_2$, 5:95 to 95:5 MeCN:H$_2$O 25 mL/min over 20 min) afforded C41allyl-C2'epiOH-methylketal-azidoAmB 5.8 (48.6 mg, 0.047 mmol, 27% yield) as a flaky yellow solid. Material with extra silyl groups remaining was also recovered (111 mg). This material was re-subjected to similar reaction conditions (assuming fully silylated 5.7 as a molecular weight: pyridine 585 μL, 7.25 mmol, 125 equiv; HF-pyr 70%, 345 μL, 19 mmol, 328 equiv; 1.2 mL:0.2 mL THF:MeOH). A second cycle and HPLC purification yielded 5.8 (152.6 mg, 152 μmol, 88% combined yield) as a yellow flaky solid.

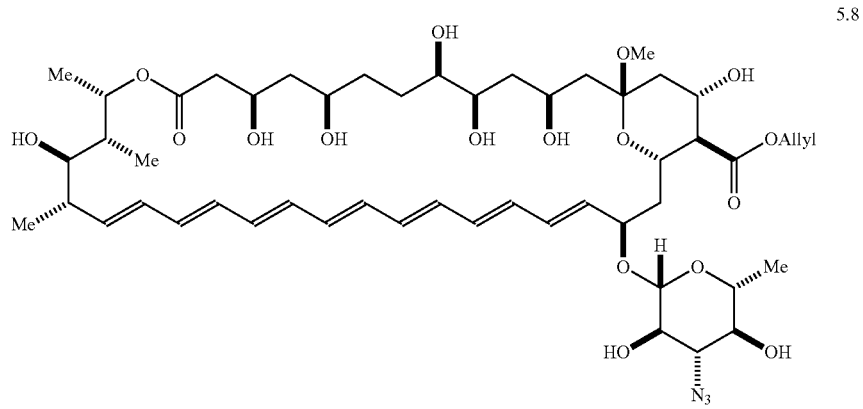
5.8
$R_f$=15.68 min ($C_{18}SiO_2$ analytical HPLC, 5:95 to 95:5 MeCN:H$_2$O over 20 min, 1 mL/min)
$^1$H NMR: (500 MHz, CD$_3$C(O)CD$_3$) δ 6.55-6.15 (m, 23H), 6.06-5.89 (m, 3H), 5.54-5.46 (m, 2H), 5.41 (dq, J=17.3, 1.7 Hz, 1H), 5.38-5.31 (m, 1H), 5.24 (dq, J=10.5, 1.5 Hz, 2H), 4.76-4.61 (m, 8H), 4.36-4.32 (m, 1H), 4.32-4.15 (m, 4H), 4.15-4.05 (m, 5H), 3.97 (dt, J=19.0, 4.2 Hz, 3H), 3.91-3.84 (m, 2H), 3.84-3.71 (m, 5H), 3.64-3.49 (m, 12H), 3.44-3.26 (m, 9H), 3.22 (d, J=6.3 Hz, 7H), 3.01 (td, J=9.0, 5.1 Hz, 2H), 2.49-2.20 (m, 8H), 2.17-2.08 (m, 3H), 2.04-1.72 (m, 13H), 1.71-1.53 (m, 16H), 1.53-1.39 (m, 12H), 1.21 (qd, J=7.2, 6.4, 3.1 Hz, 12H), 1.12 (dd, J=6.9, 3.7 Hz, 6H), 1.02 (t, J=8.0 Hz, 6H).
$^{13}$C NMR: (126 MHz, CD$_3$C(O)CD$_3$) δ 172.92, 172.30, 137.60, 136.91, 135.04, 134.98, 134.35, 133.89, 133.82, 133.76, 133.68, 133.36, 133.18, 132.79, 131.24, 118.46, 104.39, 102.54, 102.51, 78.81, 77.90, 76.00, 75.24, 75.17, 73.99, 73.54, 72.91, 71.14, 70.63, 69.47, 68.66, 68.30, 67.49, 67.18, 67.06, 65.94, 62.57, 62.36, 56.45, 48.68, 44.49, 43.60, 42.74, 42.43, 41.38, 38.46, 36.82, 33.03, 31.79, 30.66, 30.63, 30.40, 30.31, 30.25, 30.23, 30.19, 30.09, 30.07, 30.01, 27.21, 24.24, 18.97, 18.20, 17.52, 12.46.
HRMS (ESI)
Calculated for $C_{51}H_{77}N_3O_{17}$ (M+Na)$^+$: 1026.5151.
Found: 1026.5115.
Synthesis of Intermediate 5.9
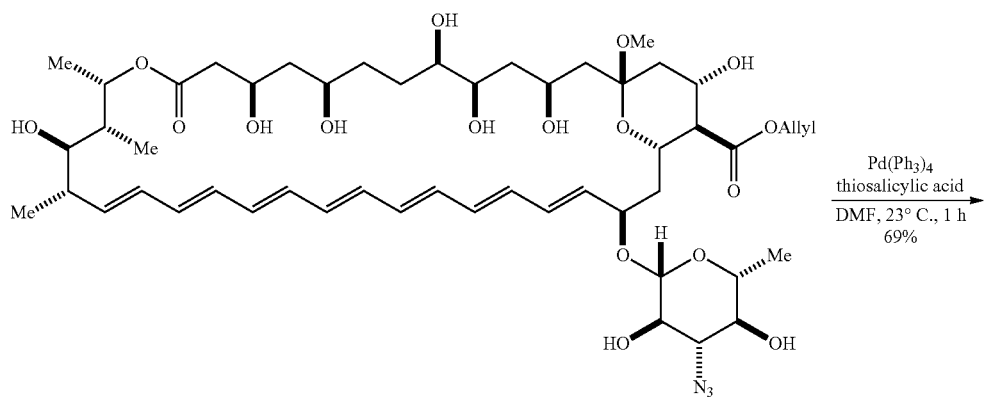
5.8

-continued

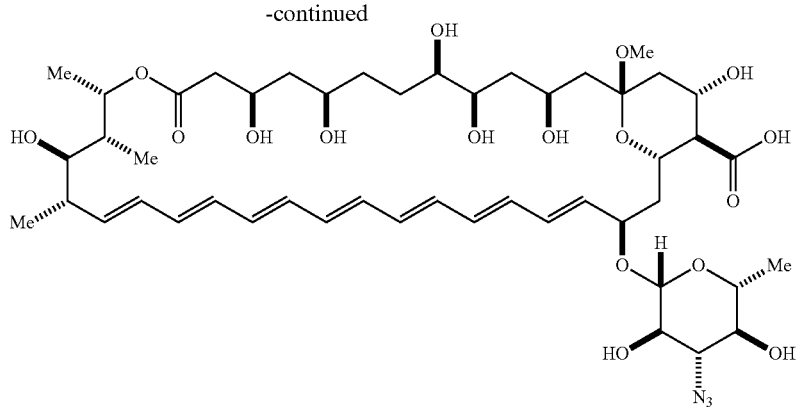

5.9

Intermediate 5.8 (104 mg, 0.135 mmol, 1.0 equiv.) was azeotropically dried with benzene (3×2 mL) placed on high vac overnight in a 20 mL iChem vial. In the glove box, Pd(PPh$_3$)$_4$ (35.9 mg, 0.03105 mmol, 30 mol %) and thiosalicylic acid (79.8 mg, 0.517 mmol, 5.0 equiv.) was added followed by DMF (3.5 mL) and sealed under Ar atmosphere and stirred for 1 h at 23° C. The reaction was transferred drop-wise into rapidly stirring Et$_2$O (100 mL). The precipitate was filtered through a 5" pipette containing a small piece of a Kim-wipe™ as a filter. The filter cake was then washed with additional Et$_2$O then eluted through the filter with DMSO. The filter was washed further with minimal DMSO. The combined DMSO fractions were lyophilized to yield 5.9 (68.9 mg, 0.714 mmol, 69%) as a yellow powder and taken on to the next reaction without additional purification. By analytical HPLC full conversion to a single peak was observed.

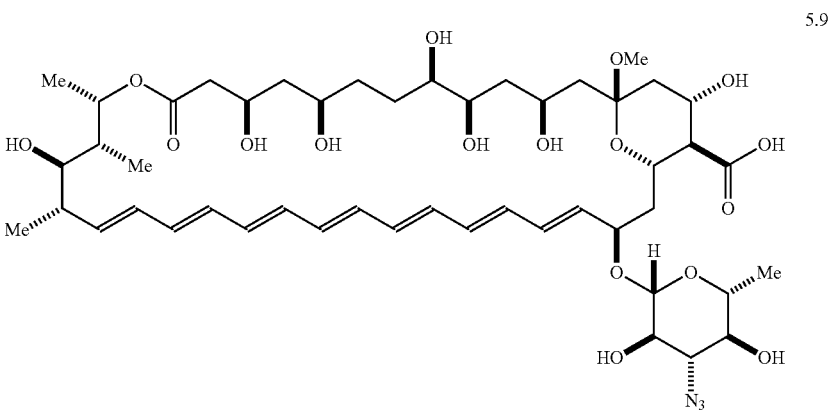

5.9

$R_f$=18.7 min (C$_{18}$SiO$_2$ analytical HPLC, 5:95 to 95:5 MeCN:H$_2$O w/0.1% formic acid over 20 min, 1 mL/min)
HRMS (ESI)

Calculated for C$_{48}$H$_{73}$N$_3$O$_{17}$ (M+Na)$^+$: 986.4838.
Found: 986.4825.

Synthesis of Intermediate 5.10

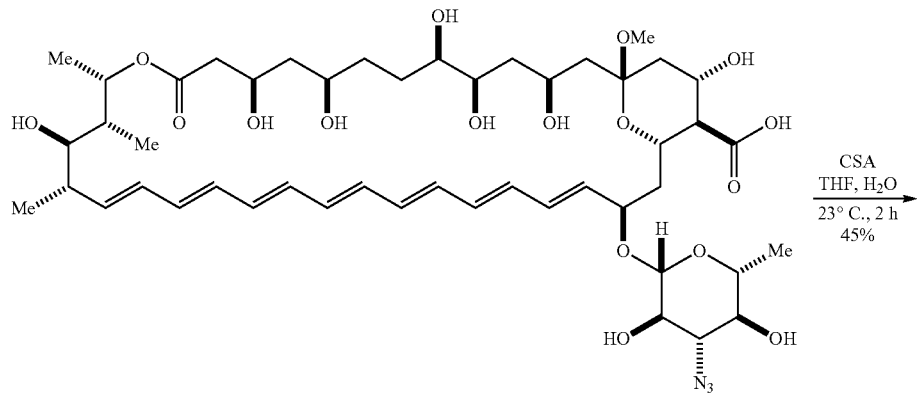

To a stirred solution of 5.9 (68.9 mg, 0.0715 mmol, 1.0 equiv.) in THF:H$_2$O (1.59 mL: 0.8 mL 2:1) in a 7 mL vial at 23° C. was added CSA (4.5 mg, 0.0178 mmol, 0.25 equiv.) and stirred for 2 h. Aqueous saturated bicarbonate (0.5 mL) was added and then filtered through HPLC filters followed by preparative reverse phase HPLC purification (C$_{18}$SiO$_2$, 5:95 to 95:5 MeCN:H$_2$O with 0.1% formic acid for 25 min at 25 mL/min) yielded 5.10 (30.8 mg, 32.2 μmol, 45%) as a yellow powder.

R$_f$=19.3 min (C$_{18}$SiO$_2$ analytical HPLC, 5:95 to 95:5 MeCN:H$_2$O over 20 min, 1 mL/min)

HRMS (ESI)

Calculated for C$_{47}$H$_{71}$N$_3$O$_{17}$ (M+Na)$^+$: 972.4681.

Found: 972.4661.

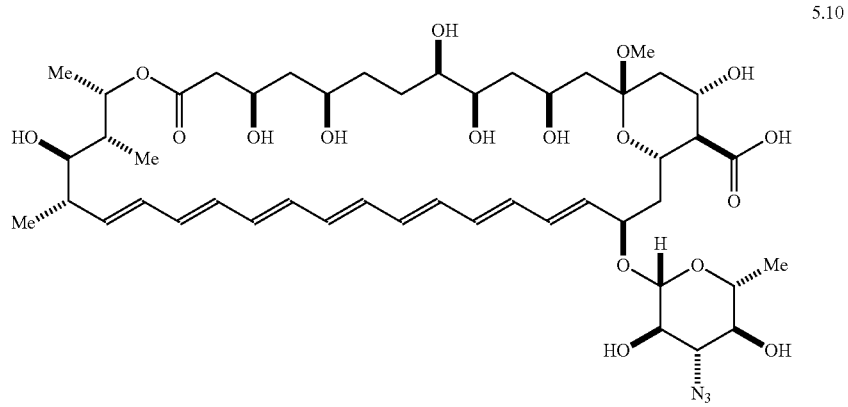

5.10

Synthesis of C2'epiAmB $R_f$=11.17 min ($C_{18}SiO_2$ analytical HPLC, 5:95 to 95:5 MeCN:$NH_4$OAc (5 mM) over 20 min, 1 mL/min)

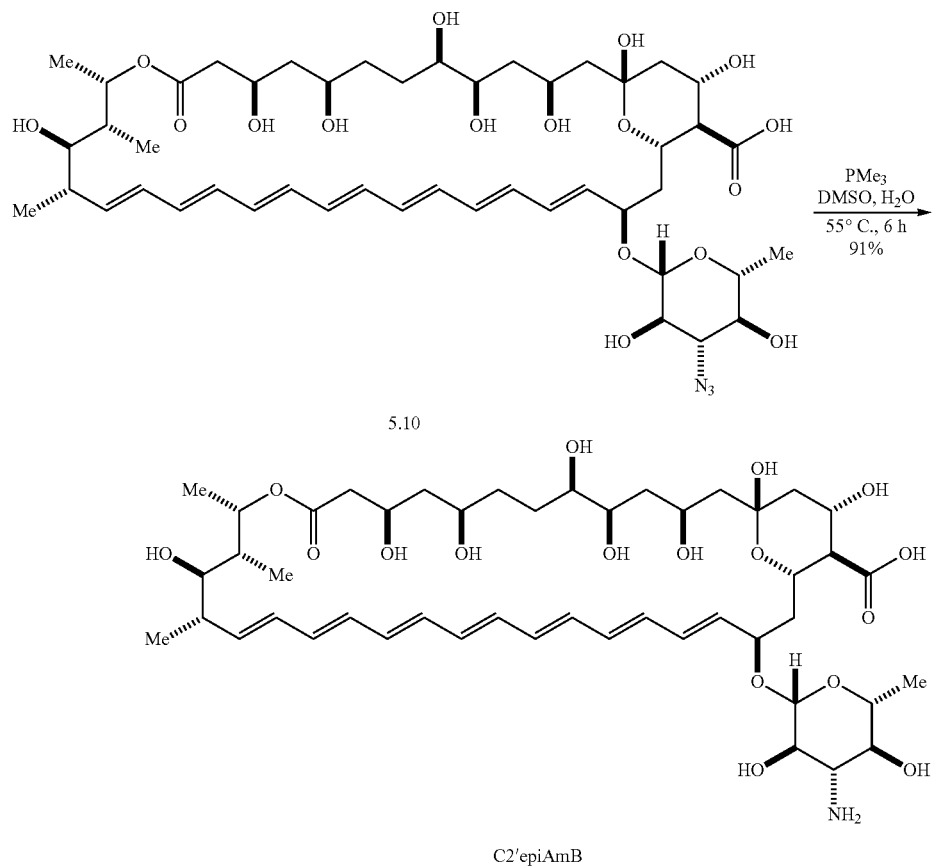

To a stirred solution of 5.10 (30.8 mg, 32.2 μmol, 1.0 equiv.) in DMSO (1.1 mL) and H₂O (58 μL, 100 equiv.) in a 7 mL vial at 23° C. under Ar atmosphere was added PMe₃ as a 1.0 M solution in THF (97 μL, 97.0 μmol, 3.0 equiv.) and then warmed to 55° C. for 6 h. The reaction was then concentrated under reduced pressure followed by preparative reverse phase HPLC purification ($C_{18}SiO_2$, 5:95 to 95:5 MeCN:$NH_4$OAc (15 mM) for 20 min at 25 mL/min) yielded C2'epiAmB (11.2 mg, 17.2 μmol, 54%) as a yellow powder.

Extinction coefficient: 92,000 cm²/mol

¹H NMR: (500 MHz, CD₃S(O)CD₃) δ 6.55-6.03 (m, 10H), 5.97 (dd, J=15.5, 8.7 Hz, 1H), 5.75 (d, J=10.9 Hz, 1H), 5.44 (dd, J=15.0, 10.1 Hz, 1H), 5.34 (s, 1H), 5.21 (d, J=7.9 Hz, 1H), 4.89-4.71 (m, 3H), 4.62 (d, J=5.7 Hz, 1H), 4.41 (d, J=6.3 Hz, 1H), 4.39-4.30 (m, 2H), 4.25 (t, J=10.5 Hz, 2H), 4.06 (s, 1H), 3.91 (d, J=10.4 Hz, 1H), 3.49 (d, J=31.6 Hz, 2H), 3.17-3.04 (m, 2H), 3.04-2.84 (m, 2H), 2.66 (d, J=11.9 Hz, 1H), 2.40 (s, 1H), 2.28 (dd, J=14.6, 7.5 Hz,

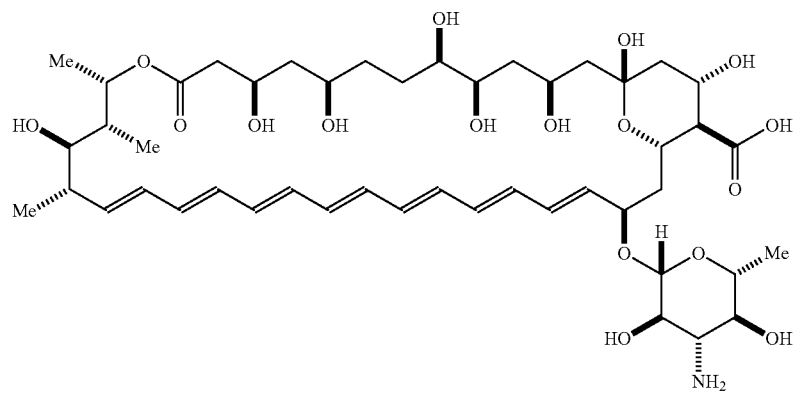

C2'epiAmB

1H), 2.17 (t, J=8.5 Hz, 2H), 2.05-1.68 (m, 5H), 1.65-1.47 (m, 5H), 1.47-1.29 (m, 7H), 1.24 (q, J=5.6, 4.6 Hz, 6H), 1.20-1.08 (m, 6H), 1.04 (t, J=7.4 Hz, 3H), 0.91 (d, J=7.1 Hz, 3H), 0.86 (td, J=7.1, 4.2 Hz, 1H).

HRMS (ESI)

Calculated for $C_{47}H_{73}NO_{17}$ (M+H)$^+$: 924.4957.

Found: 924.4960.

Synthesis of Intermediate 5.11

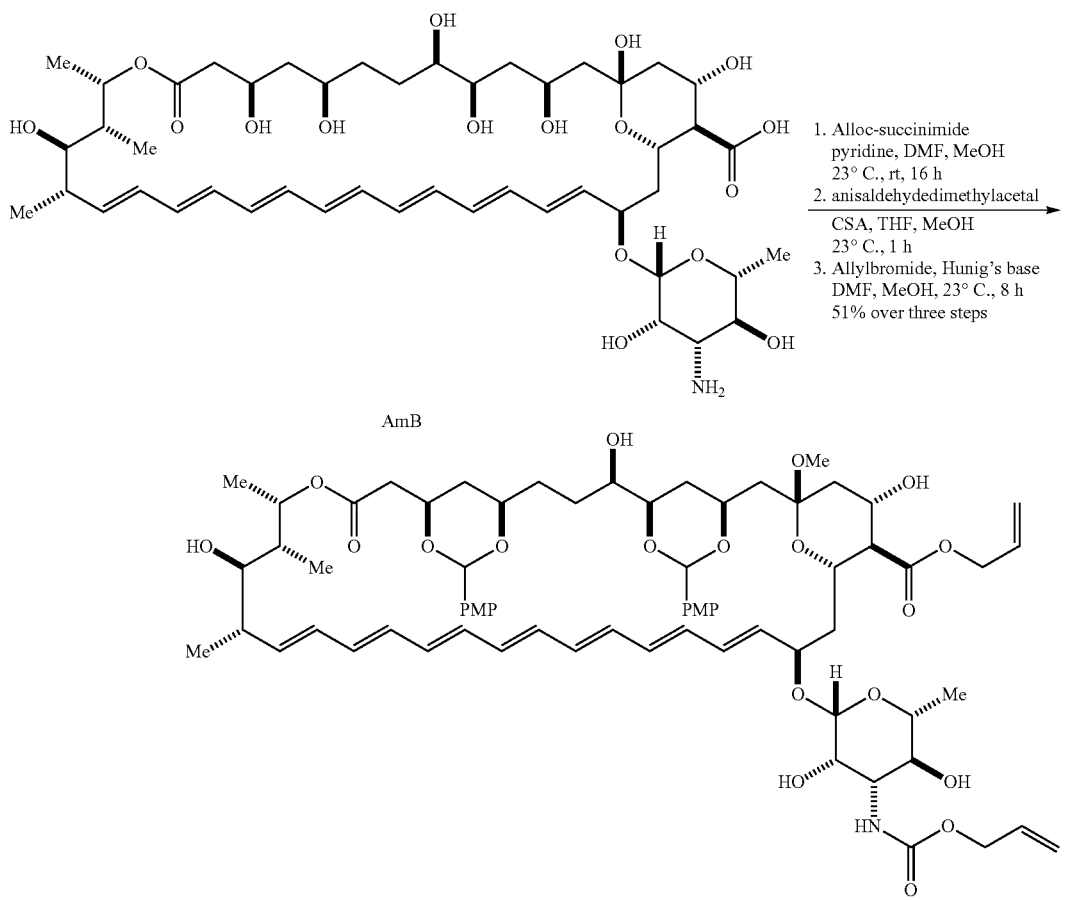

added in one portion. After stirring at 23° C. for 30 min, Et$_3$N was added (~160 μL) followed by THF (81 mL to dilute down to 0.03M). The reaction was slowly poured into rapidly stirring hexane (3.5 L). The subsequent yellow suspension was filtered through Whatman 42 filter paper and washed with Et$_2$O (3×100 mL) before the cake was allowed to fully dry. The fully dried alloc-bisPMP-methylketal (4.3 mmol, quantitative) was taken on to the subsequent reaction as a yellow powder without further purification.

To a stirred suspension of AmB (4.0 g, 4.3 mmol, 1.0 equiv.) in DMF:MeOH (75 mL: 75 mL) in a 300 mL round bottom at 23° C., was added sequentially, pyridine (5.0 mL, 50.0 mmol, 11.5 equiv.), and alloc-succinimide (2.4 g, 12.05 mmol, 2.8 equiv.). After stirring for 16 h at 23° C., the dark orange, homogeneous solution was slowly poured into rapidly stirring Et$_2$O (3.5 L). The yellow suspension was filtered through Whatman™ 42 filter paper and washed with Et$_2$O (3×100 mL) before the cake was allowed to fully dry. The fully dried alloc-AmB yellow powder (4.3 mmol, quantitative) was taken on to the subsequent reaction without further purification.

To a stirred suspension of alloc-AmB (4.3 mmol, 1.0 equiv.) in MeOH (35 mL, 0.1 M) in a 300 mL round bottom flask at 23° C. was added anisaldehyde dimethylacetal (4.0 mL, 23.5 mmol, 5.5 equiv.) and stirred for 10 min until a very fine, uniform suspension formed. CSA (250 mg, 1.08 mmol, 0.25 equiv.) as a white crystalline solid was then To a stirred suspension of alloc-bisPMP-methylketal (4.0 g, 4.3 mmol, 1.0 equiv.) in DMF:MeOH (10:1) in a 300 mL round bottom at 23° C., was added sequentially, Hunig's base (3.75 mL, 21.5 mmol, 5.0 equiv.) and allyl bromide (11.2 mL, 129.0 mmol, 30 equiv.). After stirring for 8 h at 23° C., the dark orange, homogeneous solution was transferred into a reparatory funnel containing EtOAc and deionized H$_2$O (1:1). The organic phase was washed with water (3×200 mL) followed by brine. The combined aqueous phases were extracted with EtOAc. The combined organic phases were washed with saturated brine and dried over sodium sulfate, filtered and concentrated under reduced pressure. Purification by flash chromatography (SiO$_2$, gradient elution 50:49:1 EtOAc:Hex:MeOH to 75:24:1 EtOAc:Hex:MeOH) afforded 5.12 (2.83 g, 2.19 mmol, 51%) as an orange solid.

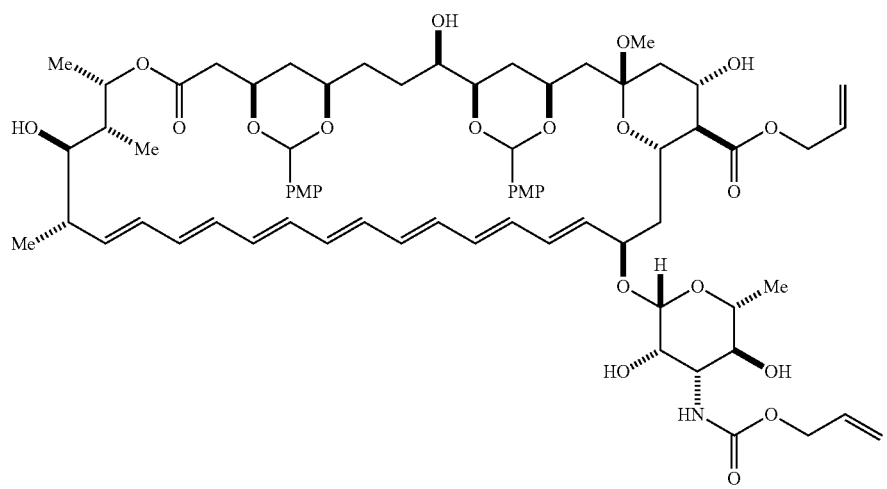
5.11
$R_f$=0.21 (50:49:1 EtOAc:Hex:MeOH)
$^1$H NMR: (500 MHz, CD$_3$C(O)CD$_3$) δ 7.43 (d, J=8.5 Hz, 2H), 7.38-7.33 (m, 2H), 6.90-6.82 (m, 4H), 6.48-6.18 (m, 11H), 6.05-5.84 (m, 3H), 5.59 (dd, J=14.3, 9.3 Hz, 1H), 5.52 (s, 1H), 5.46 (s, 1H), 5.45-5.38 (m, 1H), 5.28-5.22 (m, 1H), 4.71-4.62 (m, 3H), 4.60 (d, J=7.0 Hz, 1H), 4.53 (q, J=7.2, 4.6 Hz, 2H), 4.17 (tt, J=10.4, 6.0 Hz, 2H), 3.95 (dd, J=9.9, 6.9 Hz, 3H), 3.79 (d, J=2.9 Hz, 7H), 3.77-3.66 (m, 3H), 3.61 (td, J=9.0, 3.2 Hz, 1H), 3.45 (d, J=8.0 Hz, 1H), 3.39 (p, J=6.8 Hz, 2H), 3.33 (q, J=8.6 Hz, 3H), 3.08 (s, 2H), 2.36-2.25 (m, 3H), 1.96-1.88 (m, 2H), 1.88-1.78 (m, 3H), 1.73 (dt, J=16.4, 8.1 Hz, 3H), 1.69-1.42 (m, 8H), 1.41-1.21 (m, 28H), 1.19 (p, J=5.2 Hz, 4H), 1.13-1.08 (m, 5H), 1.02 (d, J=7.1 Hz, 4H), 0.95 (d, J=6.6 Hz, 2H), 0.87 (dt, J=12.0, 7.0 Hz, 22H).
HRMS (ESI)
Calculated for C$_{71}$H$_{95}$NO$_{21}$ (M+Na)$^+$: 1320.6294.
Found: 1320.6285.
Synthesis of Intermediate 5.12
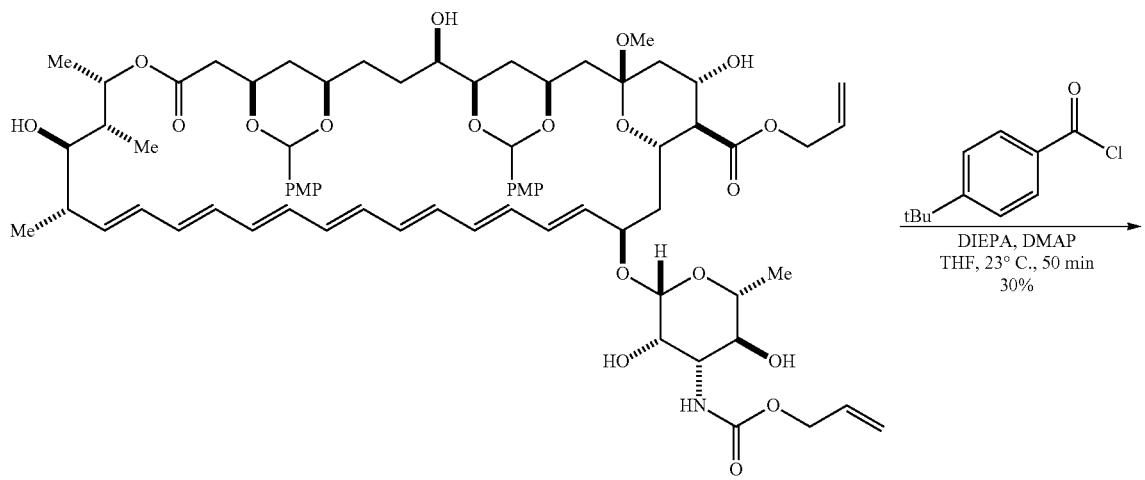
5.11

-continued

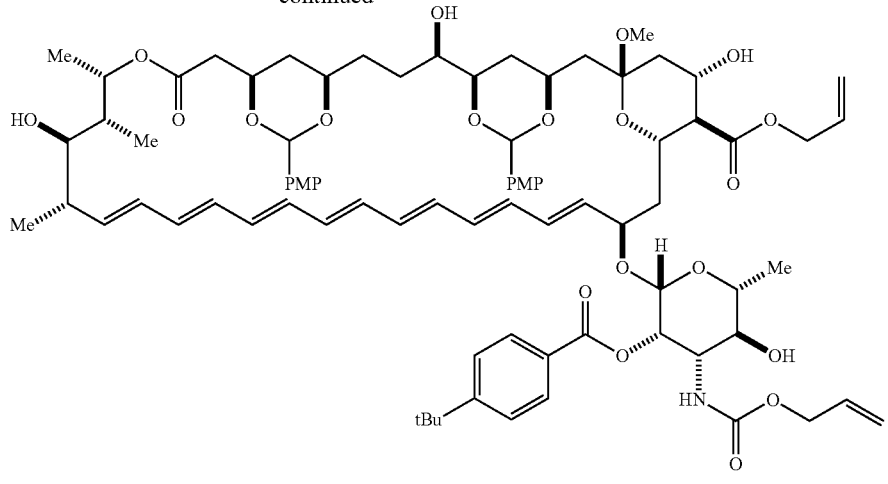

5.12

Intermediate 5.11 (2.83 g, 2.18 mmol, 1.0 equiv.) was azeotropically dried with benzene (3×10 mL) and placed on high vacuum overnight in a 300 mL round bottom flask. To intermediate 5.11 was added THF (74 mL) followed by DIPEA (0.61 mL, 3.49 mmol, 1.6 equiv). In a separate 200 mL round bottom flask was added sequentially, THF (46 mL), DMAP (426 mg, 3.49 mmol, 1.6 equiv), and drop-wise p-tertbutylbenzoylchloride (595 μL, 3.05 mmol, 1.4 equiv.) forming a fine, white suspension. Most of this suspension was slowly added drop wise via cannula to the THF, DIPEA and 5.11 solution over 50 min until a majority of the starting material was converted as judged by TLC. The reaction was diluted with EtOAc and transferred to a reparatory funnel containing aqueous saturated sodium bicarbonate and extracted with EtOAc. The combined organic phases were dried over sodium sulfate, filtered and concentrated under reduced pressure. Purification by flash chromatography (SiO$_2$, gradient eluent 65:33:2 EtOAc:Hex:MeOH isocratic) afforded 5.11 (930 g, 0.654 mmol, 30% yield) as an orange solid.

$R_f$=0.24 (65:33:2 EtOAc:Hex:MeOH)

$^1$H NMR: (500 MHz, CD$_3$C(O)CD$_3$) δ 8.07-7.89 (m, 2H), 7.64-7.48 (m, 2H), 7.38 (ddt, J=25.4, 8.0, 2.2 Hz, 4H), 6.86 (ddd, J=9.5, 4.6, 2.4 Hz, 4H), 6.46-6.11 (m, 10H), 6.10-5.96 (m, 3H), 5.96-5.82 (m, 3H), 5.82-5.65 (m, 1H), 5.58 (d, J=3.7 Hz, 1H), 5.52-5.38 (m, 2H), 5.33-5.18 (m, 1H), 5.11 (td, J=9.2, 7.5, 3.9 Hz, 1H), 4.88 (s, OH), 4.73-4.56 (m, 2H), 4.49 (t, J=5.9 Hz, 1H), 4.24-4.10 (m, 1H), 4.01-3.82 (m, 2H), 3.82-3.75 (m, 4H), 3.75-3.63 (m, 1H), 3.59 (td, J=9.6, 6.1 Hz, 1H), 3.56-3.46 (m, 1H), 3.45-3.34 (m, 1H), 2.85 (s, 1H), 2.60 (s, 1H), 2.45-2.35 (m, 1H), 2.35-2.23 (m, 1H), 2.02-1.94 (m, 1H), 1.91-1.82 (m, 1H), 1.80-1.40 (m, 6H), 1.36 (d, J=3.6 Hz, 8H), 1.32-1.26 (m, 3H), 1.22-1.15 (m, 2H), 1.12 (d, J=6.7 Hz, 2H), 1.01 (d, J=7.1 Hz, 2H).

HRMS (ESI)

Calculated for C$_{82}$H$_{107}$NO$_{22}$ (M+Na)$^+$: 1480.7182.
Found: 1480.7172.

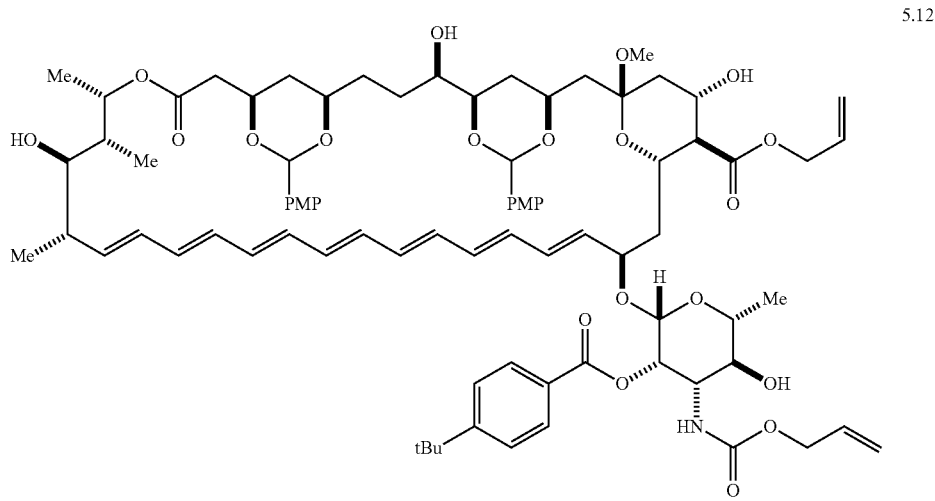

5.12

Synthesis of Intermediate 5.13

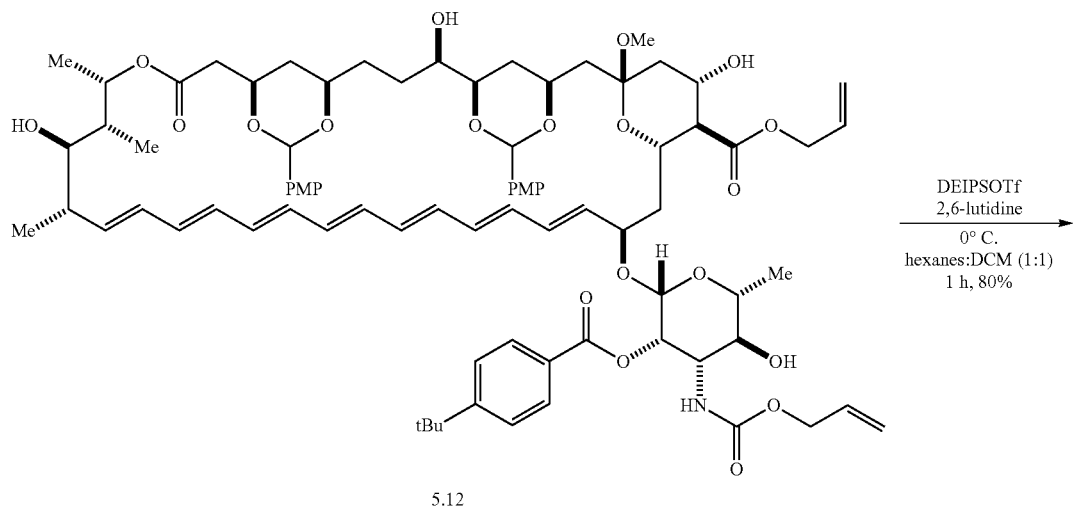

5.12

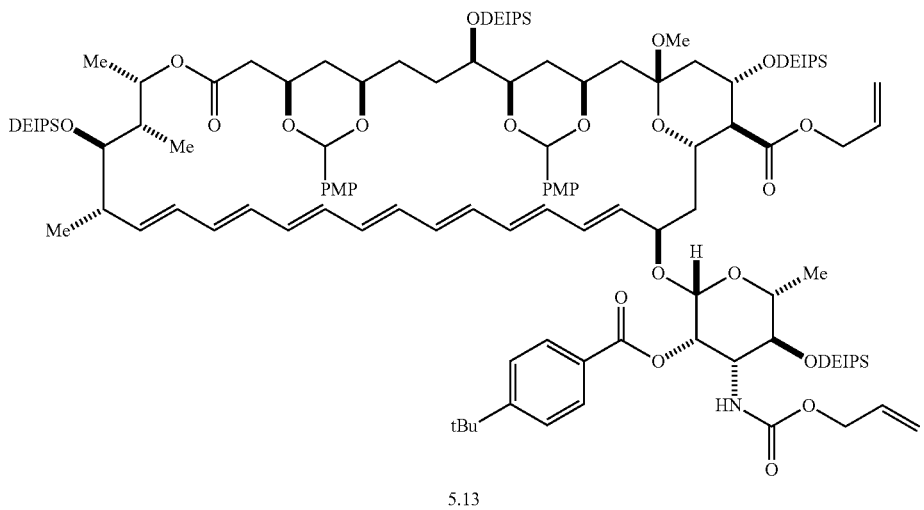

5.13

Intermediate 5.12 (910 mg, 0.624 mmol, 1.0 equiv.) was azeotropically dried with benzene (3×10 mL) and placed on high vac overnight in a 300 mL round bottom flask. To intermediate 5.13 was added DCM (10.5 mL) and hexanes (10.5 mL) followed by freshly distilled 2,6-lutidine (654 µL, 5.61 mmol, 9.1 equiv.) and cooled to 0° C. DEIPSOTf (743 µL, 3.74 mmol, 6.0 equiv.) was added dropwise over 10 min and stirred for another hour. The reaction transferred to a reparatory funnel containing $Et_2O$ and aqueous saturated bicarbonate and extracted with $Et_2O$. The combined organic phases were dried over sodium sulfate, filtered and concentrated under reduced pressure. Purification by flash chromatography ($SiO_2$, gradient eluent 1:9 EtOAc:Hex to 1:4 EtOAx:Hex) afforded 5.13 (980 mg, 0.5 mmol, 80% yield) as an orange solid.

5.13
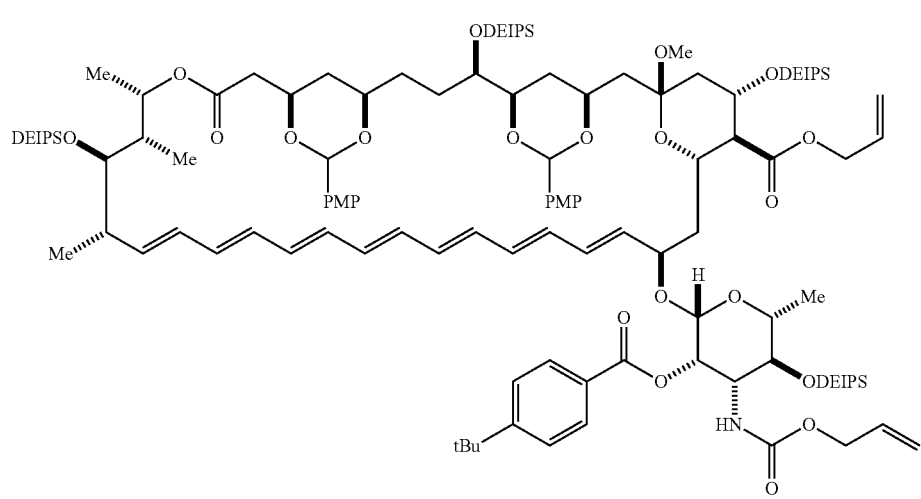
$R_f$=0.21 (1:4 EtOAc:Hex)
$^1$H NMR: (500 MHz, CD$_3$C(O)CD$_3$) δ 8.07-7.95 (m, 2H), 7.65-7.54 (m, 2H), 7.37-7.31 (m, 4H), 6.94-6.81 (m, 6H), 6.41-6.32 (m, 5H), 6.32-6.24 (m, 3H), 6.20-6.13 (m, 3H), 6.10-5.84 (m, 4H), 5.72 (ddd, J=21.6, 15.2, 6.4 Hz, 2H), 5.52 (d, J=3.3 Hz, 1H), 5.45 (q, J=1.6 Hz, OH), 5.41 (d, J=10.3 Hz, 3H), 5.34 (dt, J=10.3, 1.4 Hz, 1H), 5.27 (dq, J=17.3, 1.8 Hz, 1H), 5.13 (dq, J=10.4, 1.5 Hz, 1H), 4.91 (d, J=1.1 Hz, 1H), 4.75 (s, 1H), 4.71-4.62 (m, 2H), 4.62-4.55 (m, 2H), 4.52 (dt, J=5.6, 1.6 Hz, 2H), 4.33-4.25 (m, 1H), 4.19-4.08 (m, 1H), 4.07-3.94 (m, 1H), 3.93-3.81 (m, 3H), 3.81-3.73 (m, 10H), 3.72-3.60 (m, 4H), 3.51 (dq, J=8.8, 6.1 Hz, 1H), 2.75 (s, 3H), 2.53-2.39 (m, 2H), 2.27 (dd, J=17.7, 4.4 Hz, 1H), 2.23-2.11 (m, 2H), 2.09 (s, 7H), 1.99-1.94 (m, 1H), 1.89 (ddt, J=12.5, 8.0, 3.9 Hz, 1H), 1.78-1.56 (m, 5H), 1.56-1.41 (m, 4H), 1.37 (d, J=3.4 Hz, 14H), 1.32-1.21 (m, 6H), 1.21-1.11 (m, 7H), 1.09 (d, J=6.8 Hz, 3H), 1.07-0.76 (m, 79H), 0.76-0.65 (m, 12H), 0.61-0.49 (m, 7H), 0.43 (dqd, J=14.1, 7.9, 1.7 Hz, 5H).
$^{13}$C NMR: (126 MHz, CD$_3$C(O)CD$_3$) δ 172.60, 170.01, 166.28, 160.93, 160.80, 157.48, 157.01, 138.66, 135.17, 134.93, 134.66, 134.40, 134.27, 134.01, 133.67, 133.05, 132.92, 132.79, 132.29, 131.26, 130.93, 130.90, 129.29, 129.12, 128.87, 128.47, 127.24, 126.28, 119.43, 117.28, 114.09, 114.08, 113.99, 102.02, 101.18, 100.78, 96.73, 81.57, 75.89, 75.03, 74.97, 74.17, 73.14, 73.02, 72.98, 68.92, 66.82, 65.95, 65.84, 58.56, 57.01, 55.68, 48.58, 43.99, 42.91, 41.29, 38.08, 36.90, 35.90, 33.75, 32.97, 31.64, 30.77, 28.14, 19.27, 18.24, 18.19, 18.07, 18.01, 17.70, 17.68, 14.19, 14.17, 14.03, 13.76, 7.94, 7.90, 7.82, 7.77, 7.72, 7.71, 7.48, 7.36, 5.21, 5.10, 4.94, 4.89, 4.69, 4.44.
HRMS (ESI)
Calculated for C$_{110}$H$_{171}$NO$_{22}$ (M+Na)$^+$: 1993.1268.
Found: 1993.1189.
Synthesis of Intermediate 5.14
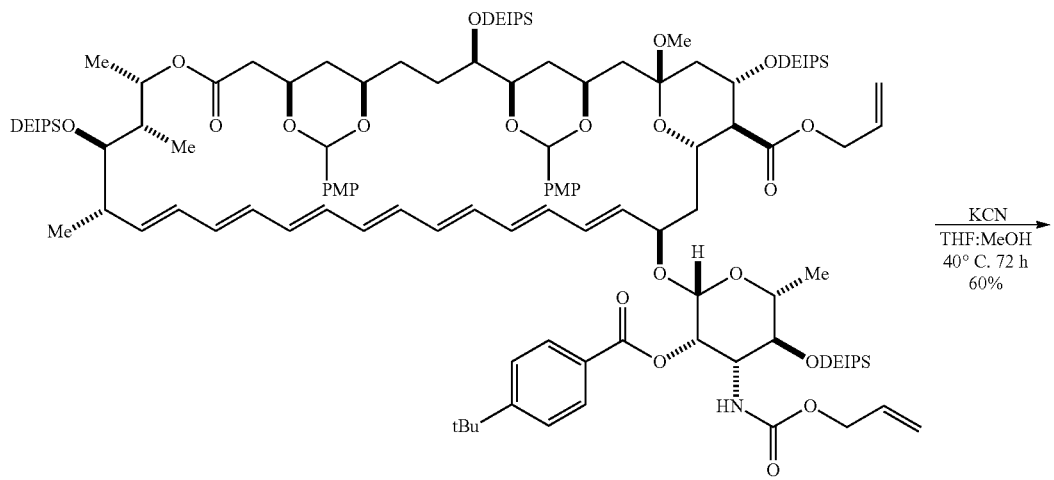
5.13

-continued

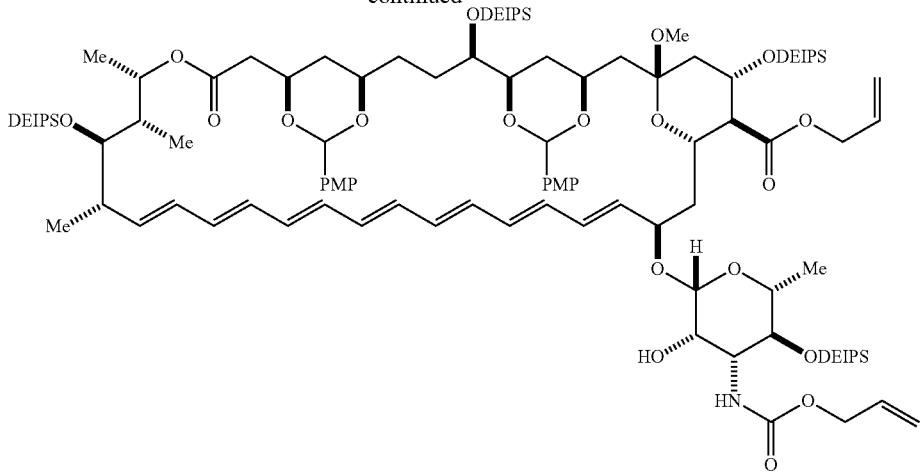

5.14

Intermediate 5.13 (980 mg, 0.497 mmol, 1.0 equiv.) was azeotropically dried with benzene (3×10 mL) and placed on high vac overnight in a 40 mL iChem. To intermediate 5.13 was added THF (6.2 mL) and MeOH (12.3 mL) followed by KCN (48.5 mg, 0.745 mmol, 1.5 equiv.) placed under Ar atmosphere and warmed to 40° C. and stirred for 72 h. The reaction transferred to a reparatory funnel containing Et$_2$O and aqueous saturated bicarbonate. The organic phase was washed with water followed by brine. The combined aqueous phases were extracted with Et$_2$O. The combined organic phases were dried over sodium sulfate, filtered and concentrated under reduced pressure. Purification by flash chromatography (SiO$_2$, gradient eluent 1:9 EtOAc:Hex to 1:4 EtOAx:Hex) afforded 5.14 (542 mg, 0.298 mmol, 60% yield) as an orange solid.

$R_f$=0.22 (3:7 EtOAc:Hex)

$^1$H NMR: (500 MHz, CD$_3$C(O)CD$_3$) δ 7.43-7.30 (m, 5H), 6.92-6.79 (m, 5H), 6.48-6.14 (m, 12H), 6.11 (dd, J=15.0, 10.0 Hz, 1H), 6.03-5.89 (m, 3H), 5.88-5.73 (m, 2H), 5.43 (d, J=3.6 Hz, 3H), 5.37 (dq, J=21.8, 1.6 Hz, 1H), 5.33-5.26 (m, 2H), 5.17 (dq, J=10.6, 1.5 Hz, 1H), 4.79 (s, 1H), 4.71-4.48 (m, 7H), 4.27 (td, J=10.6, 4.7 Hz, 1H), 4.21-4.11 (m, 1H), 3.95-3.82 (m, 4H), 3.79 (s, 4H), 3.78 (s, 4H), 3.77-3.63 (m, 6H), 3.54 (t, J=9.2 Hz, 1H), 3.38-3.26 (m, 1H), 2.49 (dd, J=17.6, 7.6 Hz, 1H), 2.43 (q, J=7.1 Hz, 1H), 2.32-2.24 (m, 3H), 1.96 (s, 3H), 1.94-1.86 (m, 2H), 1.82-1.67 (m, 3H), 1.66-1.57 (m, 2H), 1.58-1.27 (m, 7H), 1.26 (d, J=6.1 Hz, 4H), 1.23-1.10 (m, 8H), 1.10-0.86 (m, 58H), 0.86-0.76 (m, 15H), 0.70 (tdt, J=8.2, 4.4, 2.9 Hz, 11H), 0.63-0.48 (m, 5H), 0.48-0.36 (m, 4H).

HRMS (ESI)
Calculated for C$_{99}$H$_{159}$NO$_{21}$ (M+Na)$^+$: 1833.0379.
Found: 1833.0355.

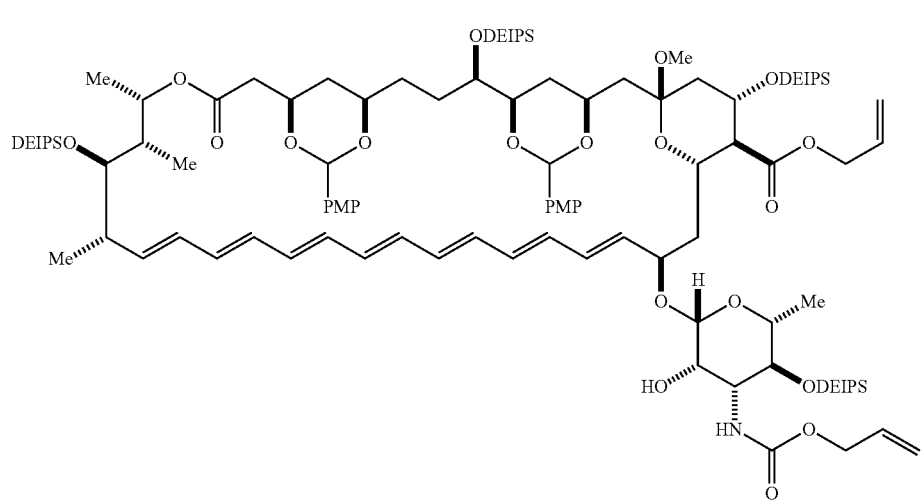

5.14

Synthesis of Intermediate 5.15

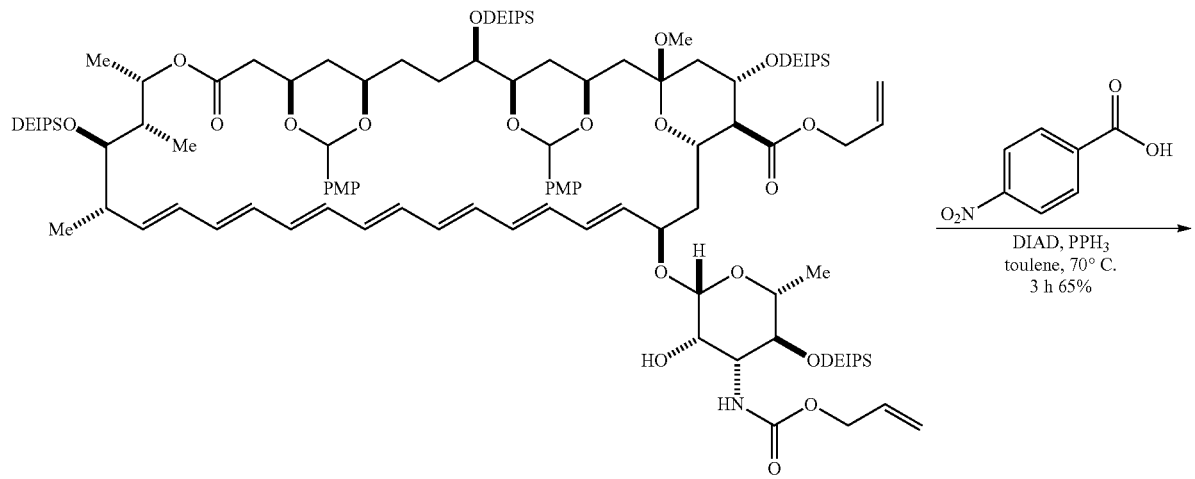

5.14

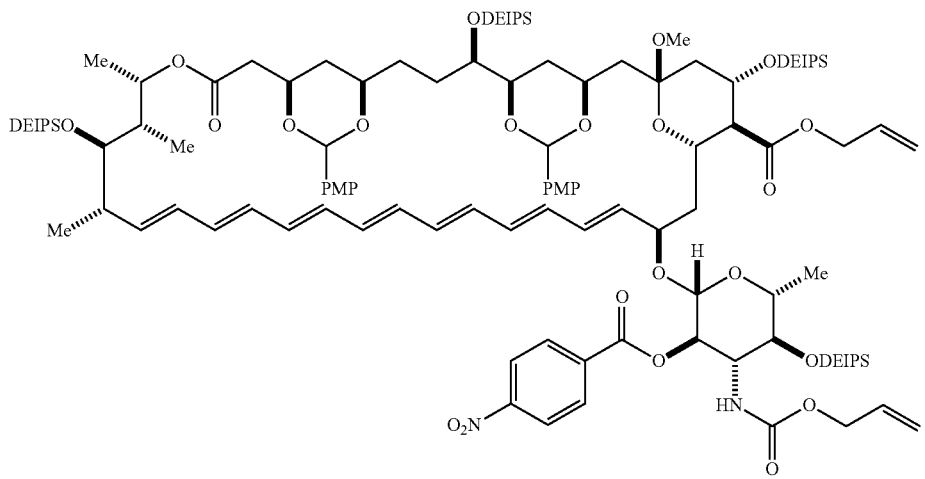

5.15

Intermediate 5.14 (271 mg, 0.15 mmol, 1.0 equiv.) was azeotropically dried with benzene (3×10 mL) and placed on high vac overnight in a 40 mL iChem. To intermediate 5.14 was added p-nitrobenzoic acid (103 mg, 0.621 mmol, 4.15 equiv), PPh$_3$ (179 mg, 0.674 mmol, 4.5 equiv.) and toluene (5 mL). The solution was cooled to 0° C. and DIAD (132 µL, 0.674 mmol, 4.5 equiv.) was added drop-wise and stirred at 0° C. for 1 h. The reaction was then heated to 70° C. for 3 h. The reaction was transferred to a reparatory funnel containing Et$_2$O and aqueous saturated sodium bicarbonate. The organic phase was washed with water followed by brine. The combined aqueous phases were extracted with Et$_2$O. The combined organic phases were dried over sodium sulfate, filtered and concentrated under reduced pressure. Purification by flash chromatography (SiO$_2$, gradient eluent 1:9 EtOAc:Hex to 1:4 EtOAx:Hex) afforded C2'epi nitrobenzoate 5.15 (80.4 mg, 40.4 µmol, 27% yield) as an orange solid.

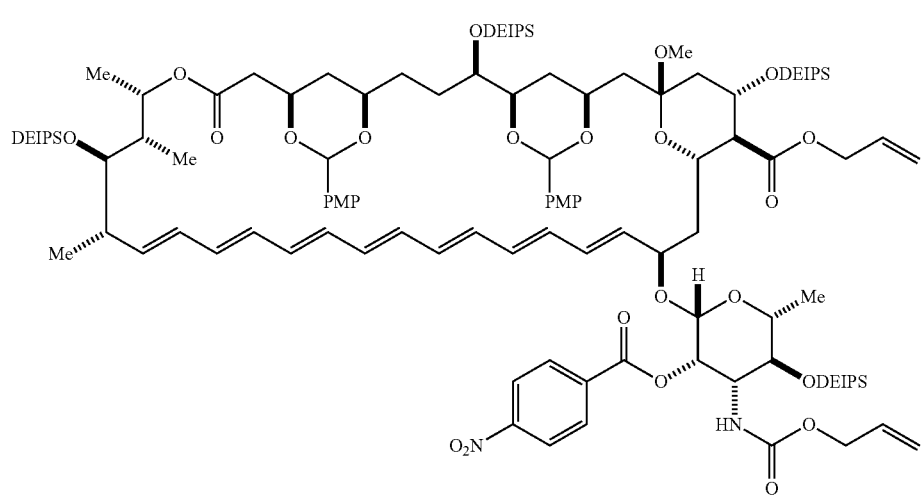
5.15
$R_f$=0.2 (1:4 EtOAc:Hex)
$^1$H NMR: (500 MHz, CD$_3$C(O)CD$_3$) δ 8.37 (s, 4H), 7.37-7.30 (m, 4H), 6.89-6.81 (m, 5H), 6.50 (d, J=9.8 Hz, 1H), 6.45-6.09 (m, 15H), 6.07-5.95 (m, 1H), 5.86 (ddd, J=19.1, 14.5, 5.8 Hz, 2H), 5.67 (ddt, J=17.3, 10.6, 5.4 Hz, 1H), 5.47-5.39 (m, 2H), 5.35 (s, 1H), 5.30 (dq, J=10.4, 1.3 Hz, 1H), 5.15 (dd, J=10.4, 7.9 Hz, 1H), 5.08 (dq, J=17.2, 1.7 Hz, 1H), 4.92 (dq, J=10.5, 1.4 Hz, 1H), 4.82 (d, J=7.8 Hz, 1H), 4.79-4.69 (m, 2H), 4.61 (qdt, J=13.1, 6.0, 1.4 Hz, 3H), 4.33 (qdt, J=13.6, 5.4, 1.5 Hz, 2H), 4.18-4.09 (m, 1H), 3.97 (td, J=10.6, 4.6 Hz, 1H), 3.90-3.81 (m, 3H), 3.77 (d, J=2.9 Hz, 8H), 3.75-3.63 (m, 7H), 3.52 (dq, J=9.0, 6.1 Hz, 1H), 2.69 (s, 3H), 2.53-2.39 (m, 2H), 2.34-2.21 (m, 1H), 2.19-2.07 (m, 2H), 2.04-1.98 (m, 1H), 1.88 (dddd, J=12.9, 10.2, 6.6, 3.8 Hz, 1H), 1.79 (d, J=15.5 Hz, 1H), 1.76-1.64 (m, 2H), 1.61 (dt, J=13.0, 2.5 Hz, 1H), 1.56-1.40 (m, 5H), 1.37-1.24 (m, 14H), 1.23-1.12 (m, 8H), 1.10-0.95 (m, 45H), 0.94-0.84 (m, 19H), 0.84-0.76 (m, 13H), 0.74-0.60 (m, 15H), 0.53 (dqd, J=26.8, 7.8, 3.2 Hz, 5H), 0.42-0.28 (m, 5H).
$^{13}$C NMR: (126 MHz, CD$_3$C(O)CD$_3$) δ 173.00, 170.05, 164.87, 160.93, 160.79, 157.06, 151.67, 138.05, 136.54, 134.87, 134.73, 134.64, 134.56, 134.45, 134.16, 133.82, 133.65, 133.35, 132.91, 132.75, 132.48, 132.40, 131.84, 130.96, 128.86, 128.47, 127.65, 124.39, 119.57, 117.11, 114.07, 113.98, 101.97, 101.21, 100.71, 98.47, 81.53, 76.09, 76.00, 75.09, 74.92, 73.67, 73.04, 72.94, 68.84, 66.84, 66.12, 65.56, 59.60, 58.12, 55.66, 55.12, 48.39, 43.94, 42.99, 41.32, 38.08, 36.35, 33.68, 32.96, 28.21, 22.01, 18.87, 18.20, 18.14, 18.00, 17.98, 17.93, 17.62, 17.60, 14.15, 14.12, 14.02, 13.67, 7.90, 7.86, 7.76, 7.73, 7.69, 7.66, 7.36, 5.15, 5.06, 4.93, 4.91, 4.88, 4.63, 4.36.
HRMS (ESI)
Calculated for C$_{106}$H$_{162}$N$_2$O$_{24}$Si$_4$ (M+Na)+: 1982.0492.
Found: 1982.0464.
Synthesis of Intermediate 5.16
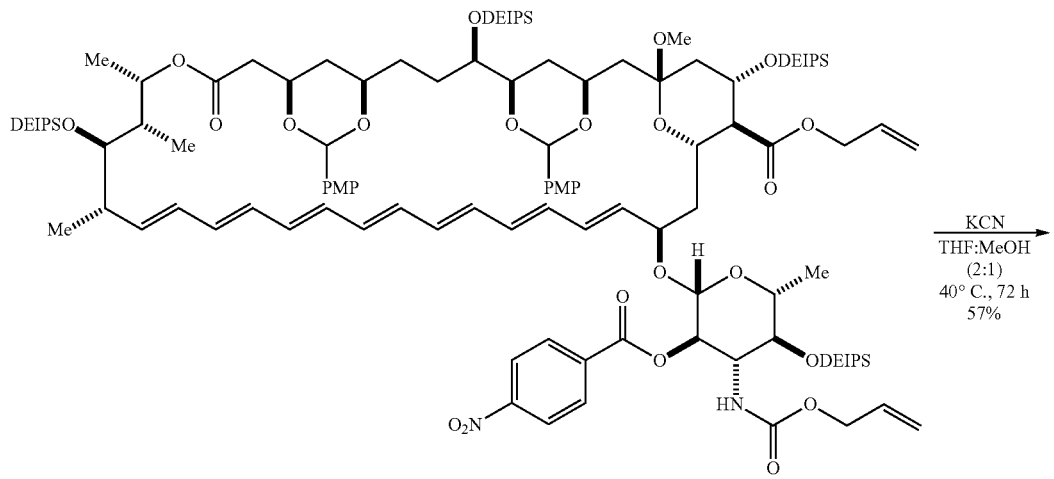
5.15

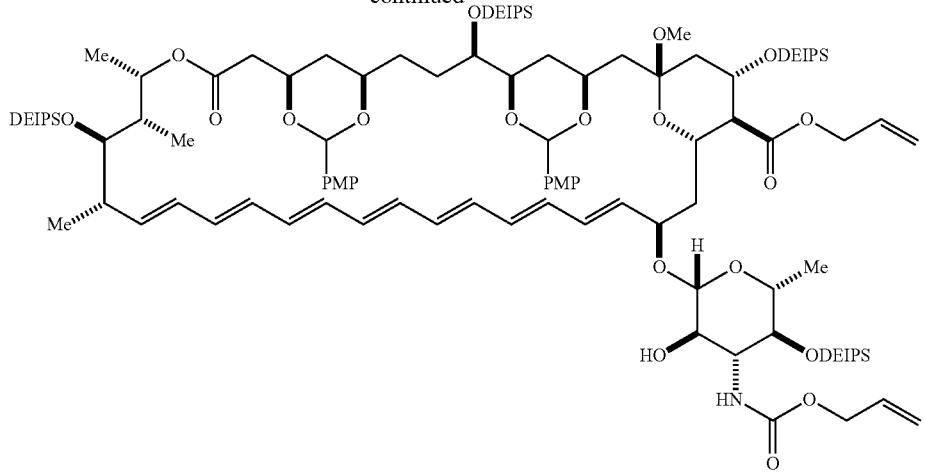

5.16

Intermediate 5.15 (80.4 g, 40.4 μmol, 1.0 equiv.) was azeotropically dried with benzene (3×10 mL) and placed on high vac overnight in a 7 mL iChem. To intermediate 5.15 was added THF (1.0 mL) and MeOH (0.5 mL) followed by KCN (4.08 mg, 61.4 μmol, 1.5 equiv.) placed under Ar atmosphere and warmed to 40° C. and stirred for 72 h. The reaction transferred to a reparatory funnel containing Et$_2$O and aqueous saturated bicarbonate. The organic phase was washed with water followed by brine. The combined aqueous phases were extracted with Et$_2$O. The combined organic phases were dried over sodium sulfate, filtered and concentrated under reduced pressure. Purification by flash chromatography (SiO$_2$, gradient eluent 1:9 EtOAc:Hex to 1:4 EtOAx:Hex) afforded 5.16 (42.6 mg, 23.4 μmol, 57% yield) as an orange solid.

$R_f$=0.2 (3:7 EtOAc:Hex)

$^1$H NMR: (500 MHz, CD$_3$C(O)CD$_3$) δ 7.43-7.32 (m, 4H), 6.87 (ddd, J=13.9, 8.9, 2.1 Hz, 4H), 6.47-6.15 (m, 13H), 6.10 (dd, J=15.1, 10.0 Hz, 1H), 6.06-5.82 (m, 3H), 5.78 (dd, J=15.1, 8.6 Hz, 1H), 5.43 (d, J=6.0 Hz, 3H), 5.36 (dt, J=31.2, 1.6 Hz, 1H), 5.31-5.25 (m, 1H), 5.16 (dt, J=10.7, 1.5 Hz, 1H), 4.81 (s, 1H), 4.66-4.55 (m, 3H), 4.51 (td, J=4.9, 3.9, 1.5 Hz, 2H), 4.37 (d, J=6.5 Hz, 1H), 4.33-4.23 (m, 1H), 4.22-4.12 (m, 1H), 4.01-3.82 (m, 3H), 3.79 (d, J=1.8 Hz, 3H), 3.78 (d, J=1.9 Hz, 3H), 3.76-3.66 (m, 4H), 3.43 (tt, J=9.2, 3.9 Hz, 3H), 3.34 (h, J=6.3 Hz, 1H), 3.05 (d, J=1.9 Hz, 3H), 2.49 (dd, J=17.6, 7.7 Hz, 1H), 2.46-2.38 (m, 1H), 2.27 (dt, J=14.3, 4.6 Hz, 3H), 2.09 (d, J=1.6 Hz, 4H), 2.01-1.93 (m, 1H), 1.93-1.85 (m, 2H), 1.85-1.77 (m, 1H), 1.73 (q, J=10.2, 9.4 Hz, 1H), 1.68-1.38 (m, 7H), 1.31 (q, J=10.9 Hz, 5H), 1.24 (t, J=5.4 Hz, 4H), 1.22-1.16 (m, 6H), 1.10-0.86 (m, 52H), 0.86-0.75 (m, 14H), 0.69 (dddd, J=13.6, 11.6, 8.0, 3.8 Hz, 10H), 0.63-0.49 (m, 4H), 0.49-0.34 (m, 4H).

$^{13}$C NMR: (126 MHz, CD$_3$C(O)CD$_3$) δ 173.37, 170.15, 160.95, 160.81, 157.34, 137.97, 134.87, 134.84, 134.77, 134.74, 134.35, 134.15, 133.96, 133.77, 133.56, 133.36, 132.90, 132.78, 132.42, 131.08, 129.69, 128.90, 128.50, 119.55, 117.30, 114.08, 114.01, 103.12, 102.07, 101.27, 100.90, 81.60, 76.29, 76.20, 75.23, 74.59, 73.32, 73.28, 72.97, 69.07, 67.63, 66.27, 65.64, 61.38, 57.67, 55.66, 48.58, 44.14, 43.33, 41.41, 38.08, 37.66, 33.73, 32.93, 30.76, 28.33, 19.26, 19.11, 18.21, 18.14, 18.05, 18.02,

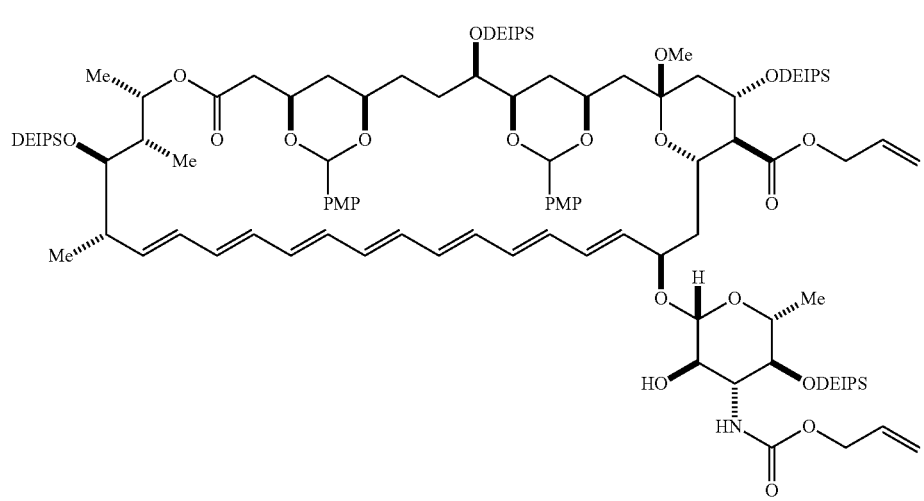

5.16

18.00, 17.69, 17.67, 14.15, 14.04, 13.72, 7.90, 7.87, 7.80, 7.78, 7.75, 7.71, 7.47, 7.45, 5.18, 5.06, 5.02, 4.96, 4.90, 4.88, 4.66, 4.43.

HRMS (ESI)
Calculated for $C_{99}H_{159}NO_{21}Si_4$ (M+Na)+: 1833.0379.
Found: 1833.0309.

Example 2

C2'epiAmB Binds Ergosterol but not Cholesterol

Figure 6A:
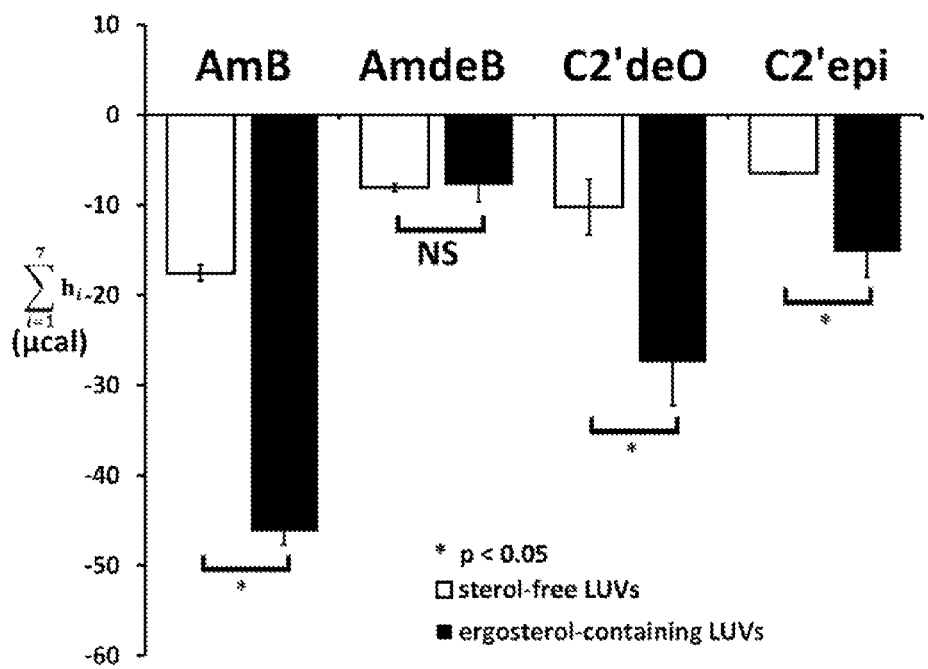
FIG. 6A is a graph depicting binding of AmB, AmdeB, C2'deOAmB, and C2'epiAmB to ergosterol. LUVs, large unilamellar vesicles; NS, not statistically significant.
Figure 6B:
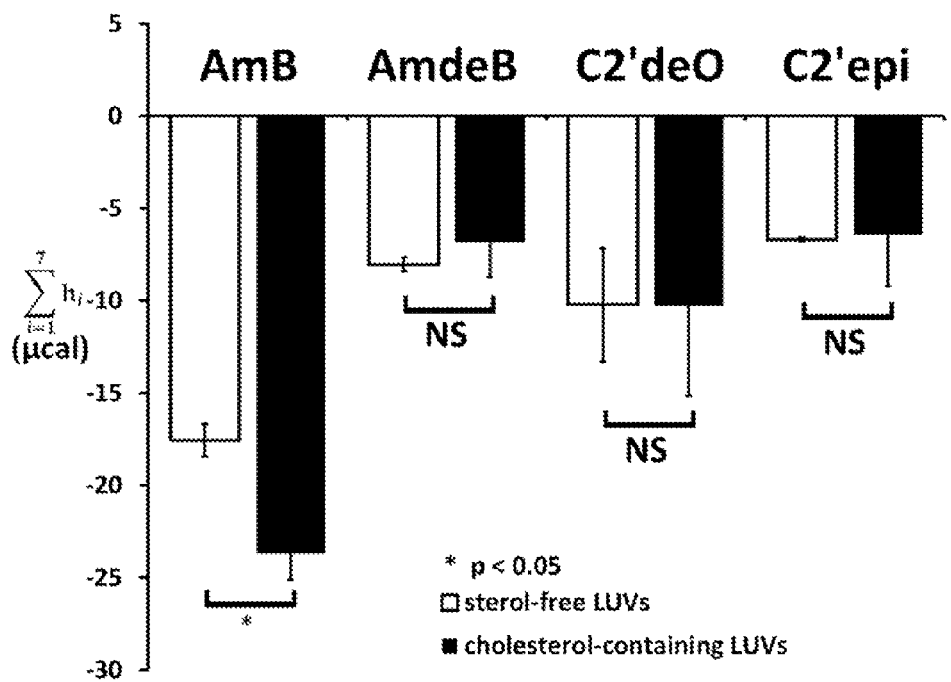
FIG. 6B is a graph depicting binding of AmB, AmdeB, C2'deOAmB, and C2'epiAmB to cholesterol. LUVs, large unilamellar vesicles; NS, not statistically significant.

The binding capability of C2'epiAmB was investigated to determine whether epimerization at CT impacts the capacity of AmB to bind ergosterol. C2'epiAmB binds to ergosterol, but not cholesterol, within the limits of the binding assay, as indicated by FIG. 6.

ITC data for C2'epiAmB is as follows:
No sterol: Total exotherm=−6.70±0.11 µcal.
10% ergosterol: Total exotherm=−15.24±1.66 µcal.
10% cholesterol: Total exotherm=−6.43±2.80 µcal.

Exemplary methods of conducting the binding assay are described below.

Isothermal Titration calorimetry (ITC)

In an optimized isothermal titration calorimetry (ITC)-based assay, an aqueous solution of AmB was titrated with a suspension of large unilamellar vesicles (LUVs) comprised of only 1-palmitoyl-2-oleoyl-sn-glycero-3-phosphocholine (POPC), and the net exotherm was recorded. The titration was repeated using POPC LUVs containing 10% ergosterol. A significant increase in net exotherm was observed when switching to ergosterol-containing LUVs, indicating a direct AmB-sterol binding interaction. The titration was repeated using C2'epiAmB. A significant increase in net exotherm indicated a retained capacity for the epimeric derivative to bind ergosterol. The ITC assay was also conducted with cholesterol in place of ergosterol. C2'epiAmB was not found to bind to cholesterol.

General Information

Experiments were performed using a NanoITC isothermal titration calorimeter (TA Instruments, Wilmington, Del.). Solutions of the compounds to be tested were prepared by diluting a 60.0 mM stock solution of the compound in DMSO to 600 µM with K buffer (5.0 mM HEPES/KHEPES, pH=7.4). The final DMSO concentration in the solution was 1% v/v. Large unilamellar vesicles comprised of only 1-palmitoyl-2-oleoyl-sn-glycero-3-phosphocholine (POPC LUVs) were prepared and phosphorus and ergosterol content was quantified as described below. The LUV solutions were diluted with buffer and DMSO to give a final phospholipid concentration of 12.0 mM in a 1% DMSO/K buffer solution. Immediately prior to use, all solutions were incubated at 37° C. for 30 minutes and degassed under vacuum at 37° C. for 10 minutes. The reference cell of the instrument (volume=0.190 mL) was filled with a solution of 1% v/v DMSO/K buffer.

LUV Preparation

Palmitoyl oleoyl phosphatidylcholine (POPC) was obtained as a 20 mg/mL solution in $CHCl_3$ from Avanti Polar Lipids (Alabaster, Ala.) and was stored at −20° C. under an atmosphere of dry argon and used within 1 month. A 4 mg/mL solution of ergosterol in $CHCl_3$ was prepared monthly and stored at 4° C. under an atmosphere of dry argon. Prior to preparing a lipid film, the solutions were warmed to ambient temperature to prevent condensation from contaminating the solutions. A 13×100 mm test tube was charged with 800 µL POPC and 230 µL of the ergosterol solution. For cholesterol-containing liposomes, a 13×100 mm test tube was charged with 800 µL POPC and 224 µL of the ergosterol solution. For sterol-free liposomes, a 13×100 mm test tube was charged with 800 µL POPC. The solvent was removed with a gentle stream of nitrogen and the resulting lipid film was stored under high vacuum for a minimum of eight hours prior to use. The film was then hydrated with 1 mL of K buffer and vortexed vigorously for approximately 3 minutes to form a suspension of multilamellar vesicles (MLVs). The resulting lipid suspension was pulled into a Hamilton (Reno, Nev.) 1 mL gastight syringe and the syringe was placed in an Avanti Polar Lipids Mini-Extruder. The lipid solution was then passed through a 0.20 µm Millipore (Billerica, Mass.) polycarbonate filter 21 times, the newly formed large unilamellar vesicle (LUV) suspension being collected in the syringe that did not contain the original suspension of MLVs to prevent the carryover of MLVs into the LUV solution.

Determination of Phosphorus Content

Determination of total phosphorus was adapted from the report of Chen and coworkers. Chen, P S et al. (1956) *Anal. Chem.* 28:1756. The LUV solution was diluted tenfold with K buffer and three 10 µL samples of the diluted LUV suspension were added to three separate 7 mL vials. Subsequently, the solvent was removed with a stream of $N_2$. To each dried LUV film, and a fourth vial containing no lipids that was used as a blank, was added 450 µL of 8.9 M $H_2SO_4$. The four samples were incubated open to ambient atmosphere in a 225° C. aluminum heating block for 25 min and then removed to 23° C. and cooled for 5 minutes. After cooling, 150 µL of 30% w/v aqueous hydrogen peroxide was added to each sample, and the vials were returned to the 225° C. heating block for 30 minutes. The samples were then removed to 23° C. and cooled for 5 minutes before the addition of 3.9 mL water. Then 500 µL of 2.5% w/v ammonium molybdate was added to each vial and the resulting mixtures were then vortexed briefly and vigorously five times. Subsequently, 500 µL of 10% w/v ascorbic acid was added to each vial and the resulting mixtures were then vortexed briefly and vigorously five times. The vials were enclosed with a PTFE lined cap and then placed in a 100° C. aluminum heating block for 7 minutes. The samples were removed to 23° C. and cooled for approximately 15 minutes prior to analysis by UV/Vis spectroscopy. Total phosphorus was determined by observing the absorbance at 820 nm and comparing this value to a standard curve obtained through this method and a standard phosphorus solution of known concentration.

Determination of Ergosterol Content

Ergosterol content was determined spectrophotometrically. A 50 µL portion of the LUV suspension was added to 450 µL 2:18:9 hexane:isopropanol:water (v/v/v). Three independent samples were prepared and then vortexed vigorously for approximately one minute. The solutions were then analyzed by UV/Vis spectroscopy and the concentration of ergosterol in solution was determined by the extinction coefficient of 10400 L $mol^{-1}$ $cm^{-1}$ at the $UV_{max}$ of 282 nm and was compared to the concentration of phosphorus to determine the percent sterol content. The extinction coefficient was determined independently in the above ternary solvent system. LUVs prepared by this method contained between 7 and 14% ergosterol.

Titration Experiment

Titrations were performed by injecting the LUV suspension at ambient temperature into the sample cell (volume=0.191 mL) which contained the 600 µM solution of the compound in question at 25° C. The volume of the first injection was 0.23 µL. Consistent with standard procedure (Heerklotz, H et al. (2000) *Biochim. Biophys. Acta* 1508:69), due to the large error commonly associated with the first injection of ITC experiments, the heat of this injection was not included in the analysis of the data. Next, six 7.49 µL injections of the LUV suspension were performed. The spacing between each injection was 720 seconds to ensure that the instrument would return to a stable baseline before the next injection was made. The rate of stirring for each experiment was 300 rpm.

Data Analysis

NanoAnalyze software (TA Instruments) was used for baseline determination and integration of the injection heats, and Microsoft Excel was used for subtraction of dilution heats and the calculation of overall heat evolved. To correct for dilution and mixing heats, the heat of the final injection from each run was subtracted from all the injection heats for that particular experiment. See, for example, to Welscher, Y M et al. (2008) *J. Biol. Chem.* 283:6393. By this method, the overall heat evolved during the experiment was calculated using the following formula:

$$"cal_{overall} = \sum_{i=1}^{n} (\Delta h_{injection}^i - \Delta h_{injection}^n)$$

where i=injection number, n=total number of injections, $\Delta h_{injection}^i$=heat of the $i^{th}$ injection, $\Delta h_{injection}^n$=the heat of the final injection of the experiment.

Example 3

C2'epiAmB Exerts Antifungal Activity In Vitro

The activity of AmB, C2'deOAmB, and C2'epiAmB against two ergosterol-containing strains of yeast, *S. cerevisiae* and *C. albicans*, was tested. *C. albicans* represents the most common cause of life-threatening systemic fungal infections in humans. As shown in FIG. 5, C2'epiAmB demonstrated potent antifungal activity against both *S. cerevisiae* (MIC=2 µM) and *C. albicans* (MIC=2 µM).

Exemplary methods for antifungal activity assays are as follows:

Growth Conditions for *S. cerevisiae*

*S. cerevisiae* was maintained with yeast peptone dextrose (YPD) growth media consisting of 10 g/L yeast extract, 20 g/L peptone, 20 g/L dextrose, and 20 g/L agar for solid media. The media was sterilized by autoclaving at 250° F. for 30 min. Dextrose was subsequently added as a sterile 40% w/v solution in water (dextrose solutions were filter sterilized). Solid media was prepared by pouring sterile media containing agar (20 g/L) onto Corning (Corning, N.Y.) 100×20 mm polystyrene plates. Liquid cultures were incubated at 30° C. on a rotary shaker and solid cultures were maintained at 30° C. in an incubator.

Growth Conditions for *C. albicans*

*C. albicans* was cultured in a similar manner to *S. cerevisiae* except both liquid and solid cultures were incubated at 37° C.

Broth Microdilution Minimum Inhibitory Concentration (MIC) Assay

The protocol for the broth microdilution assay was adapted from the Clinical and Laboratory Standards Institute document M27-A2. Clinical and Laboratory Standards Institute. Reference Method for Broth Dilution Antifungal Susceptibility Testing, M27-A2, Approved Standard $2^{nd}$ Ed. Vol. 22, Number 15, 2002. 50 mL of YPD media was inoculated and incubated overnight at either 30° C. (*S. cerevisiae*) or 37° C. (*C. albicans*) in a shaker incubator. The cell suspension was then diluted with YPD to an $OD_{600}$ of 0.10 (~5×10$^5$ cfu/mL) as measured by a Shimadzu (Kyoto, Japan) PharmaSpec UV-1700 UV/Vis spectrophotometer. The solution was diluted 10-fold with YPD, and 195 µL aliquots of the dilute cell suspension were added to sterile Falcon (Franklin Lakes, N.J.) Microtest 96-well plates in triplicate. Compounds were prepared either as 400 µM (AmB, C2'deOAmB) or 2 mM (AmdeB) stock solutions in DMSO and serially diluted to the following concentrations with DMSO: 1600, 1200, 800, 400, 320, 240, 200, 160, 120, 80, 40, 20, 10 and 5 µM. 5 µL aliquots of each solution were added to the 96-well plate in triplicate, with each column representing a different concentration of the test compound. The concentration of DMSO in each well was 2.5% and a control well to confirm viability using only 2.5% DMSO was also performed in triplicate. This 40-fold dilution gave the following final concentrations: 50, 40, 30, 20, 10, 8, 6, 4, 1, 0.5, 0.25 and 0.125 µM. The plates were covered and incubated at 30° C. (*S. cerevisiae*) or 37° C. (*C. albicans*) for 24 hours prior to analysis. The MIC was determined to be the concentration of compound that resulted in no visible growth of the yeast. The experiments were performed in duplicate and the reported MIC represents an average of two experiments.

Example 4

C2'epiAmB is not Toxic to Human Cells In Vitro

Finally, the activity of AmB, C2'deOAmB, and C2'epiAmB was probed against human cells. Two of the most important toxic side effects associated with AmB are anemia and nephrotoxicity caused by damage to red blood cells and renal proximal tubule cells, respectively.[5a,15] Consistent with literature precedent, AmB causes 90% hemolysis of human red blood cells at a concentration of 8.5 µM. This is defined as the minimum hemolytic concentration (MHC). In stark contrast, we found that the corresponding MHCs for C2'deOAmB and C2'epiAmB, both of which do not bind cholesterol, to be >500 µM (FIG. 5). Similarly, AmB causes 90% loss of cell viability of primary human renal proximal tubule epithelial cells at a concentration of 2.4 µM (the minimum toxic concentration (MTC)). Again, in stark contrast to AmB, both C2'deOAmB and C2'epiAmB showed no evidence of toxicity up to their limits of solubility.[16]

Exemplary methods for toxicity assays are as follows:

Hemolysis Assays

Erythrocyte Preparation

The protocol for the hemolysis assay was adapted from the report of Paquet and coworkers. Paquet, V et al. (2008) *Chem. Eur. J.* 14:2465-2481. Whole human blood (sodium heparin) was purchased from Bioreclamation LLC (Westbury, N.Y.) and stored at 4° C. and used within two days of receipt. To a 2.0 mL Eppendorf tube, 1 mL of whole human blood was added and centrifuged at 10,000 g for 2 minutes. The supernatant was removed and the erythrocyte pellet was washed with 1 mL of sterile saline and centrifuged at 10,000 g for 2 minutes. The saline wash was repeated for a total of three washes. The erythrocyte pellet was suspended in 1 mL of RBC buffer (10 mM $NaH_2PO_4$, 150 mM NaCl, 1 mM $MgCl_2$, pH 7.4) to form the erythrocyte stock suspension.

Minimum Hemolysis Concentration (MHC) Assay

Compounds were prepared as 1.03 mM (AmB) or 12.8 mM (C2'deOAmB and C2'epiAmB) stock solutions in DMSO and serially diluted to the following concentrations with DMSO: 7689, 5126, 2563, 2050, 1538, 1025, 769, 513, 384, 256, 205, 154, 103, 77, 51, 26 µM. To a 0.2 mL PCR tube, 24 µL of RBC buffer and 1 µL of compound stock solution were added, which gave final concentrations of 500, 300, 200, 100, 80, 60, 40, 30, 20, 15, 10, 8, 6, 4, 3, 2, 1 µM. Positive and negative controls were prepared by adding 1 µL of DMSO to MilliQ water or RBC buffer, respectively to 0.2 mL PCR tube. To each PCR tube, 0.63 µL of the erythrocyte stock suspension was added and mixed by inversion. The samples were incubated at 37° C. for 2 hours. The samples were mixed by inversion and centrifuged at 10,000 g for 2 minutes. 15 µL of the supernatant from each sample was added to a 384-well place. Absorbances were read at 540 nm using a Biotek H1 Synergy Hybrid Reader (Wanooski, Vt.). Experiments were performed in triplicate and the reported MHC represents an average of three experiments.

Data Analysis

Percent hemolysis was determined according to the following equation:

$$\% \text{ hemolysis} = \frac{\text{Abs.}_{sample} - \text{Abs.}_{neg.}}{\text{Abs.}_{pos.} - \text{Abs}_{neg.}} \times 100\%$$

Concentration vs. percent hemolysis was plotted and fitted to 4-parameter logistic (4PL) dose response fit using OriginPro 8.6. Sebaugh, J L (2011) *Pharmaceut. Statist.* 10:128-134. The MHC was defined as the concentration to cause 90% hemolysis.

WST-8 Cell Proliferation Assays

Primary Renal Proximal Tubule Epithelial Cells Preparation

Primary human renal proximal tubule epithelial cells (RPTECs) were purchased from ATCC (Manassas, Va.) and immediately cultured upon receipt. Complete growth media was prepared using renal epithelial cell basal medium (ATCC, PCS-400-030), renal epithelial cell growth kit (ATCC, PCS-400-040), and penicillin-streptomycin (10 units/mL and 10 µg/mL). Complete media was stored at 4° C. in the dark and used within 28 days. Primary RPTECs were grown in $CO_2$ incubator at 37° C. with an atmosphere of 95% air/5% $CO_2$.

WST-8 Reagent Preparation

WST-8 cell proliferation assay kit (Ser. No. 10/010,199) was purchased from Cayman Chemical Company (Ann Arbor, Mich.) and stored at −20° C. and used within 6 months of receipt. WST-8 reagent and electron mediator solution were thawed and mixed to prepare the WST-8 reagent solution. The solution was stored at −20° C. and used within one week.

WST-8 Assay

A suspension of primary RPTECs in complete growth media was brought to a concentration of $1 \times 10^5$ cells/mL. A 96-well plate was seeded with 99 µL of the cell suspension and incubated at 37° C. with an atmosphere of 95% air/5% $CO_2$ for 3 hours. Positive and negative controls were prepared by seeding with 100 µL of the cell suspension or 100 µL of the complete media. Compounds were prepared as 5 mM (AmB), 20 mM (C2'deOAmB), and 50 mM (C2'epiAmB) stock solutions in DMSO and serially diluted to the following concentrations with DMSO: 50000, 40000, 30000, 20000, 10000, 8000, 6000, 4000, 3000, 2000, 1500, 1000, 800, 600, 400, 300, 200, 100, 50, 25, 10, 5, 2.5, 1, 0.5, 0.25, and 0.1 µM. 1 µL aliquots of each solution were added to the 96-well plate in triplicate, with each column representing a different concentration of the test compound. The 96-well plate was incubated at 37° C. with an atmosphere of 95% air/5% $CO_2$ for 24 hours. After incubation, the media was aspirated and 100 µL of serum-free media was added and 10 µL of the WST-8 reagent solution was added to each well. The 96-well plate was mixed in a shaking incubator at 200 rpm for 1 minute and incubated at 37° C. with an atmosphere of 95% air/5% $CO_2$ for 2 hours. Following incubation, the 96-well plate was mixed in a shaking incubator at 200 rpm for 1 minute and absorbances were read at 450 nm using a Biotek H1 Synergy Hybrid Reader (Wanooski, Vt.). Experiments were performed in triplicate and the reported cytotoxicity represents an average of three experiments.

Data Analysis

Percent hemolysis was determined according to the following equation:

$$\% \text{ hemolysis} = \frac{\text{Abs.}_{sample} - \text{Abs.}_{neg.}}{\text{Abs.}_{pos.} - \text{Abs}_{neg.}} \times 100\%$$

Concentration vs. percent hemolysis was plotted and fitted to 4-parameter logistic (4PL)[8] dose response fit using OriginPro 8.6. The MTC was defined as the concentration to cause 90% loss of cell viability.

Microscopy

Cells were imaged using an AMG (Bothell, Wash.) EVOS fl Microscope. Images were taken using transmitted light at 10× objective.

Example 5

In Vivo Assessment of Biological Activity

Figure 7:
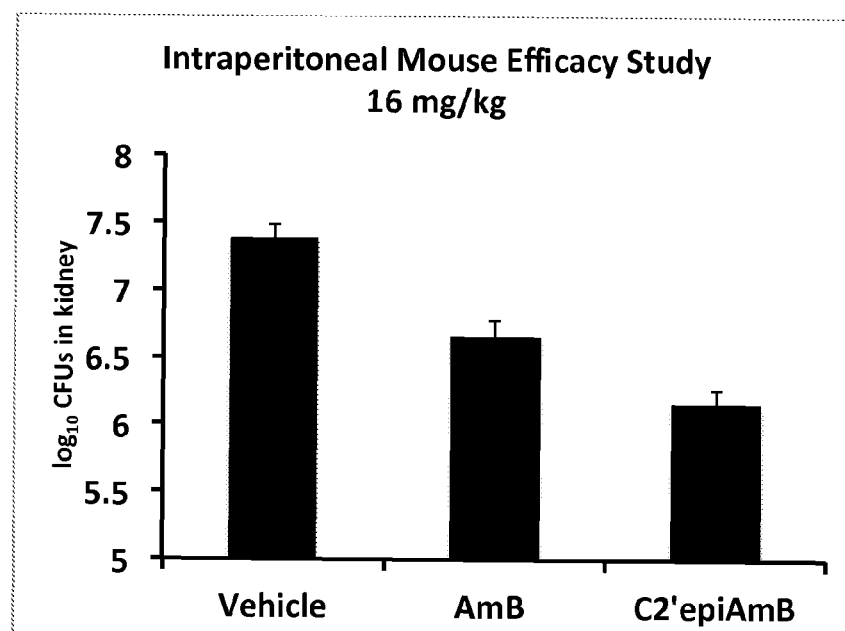
FIG. 7 is a bar graph depicting kidney fungal load (colony forming units, CFUs) in neutropenic mice inoculated intravenously with *C. albicans*, and then treated two hours later with a single intraperitoneal dose of vehicle or 16 mg/kg AmB or C2'epiAmB.

The antifungal efficacy of C2'epiAmB was tested in a mouse model of disseminated candidiasis. In this experiment neutropenic mice were infected with *C. albicans* via their tail veins, and then 2 hours post infection the mice were treated with a single intraperitoneal injection of 16 mg/kg AmB or C2'epiAmB. Then at 24 hours post infection the mice were sacrificed, and the fungal burden present in their kidneys was quantified. Results are shown in FIG. 7. C2'epiAmB was more effective than AmB at reducing the fungal burden present in the kidneys. Relative to AmB, C2'epiAmB reduced the fungal burden by 0.5 log units.

Figure 8:
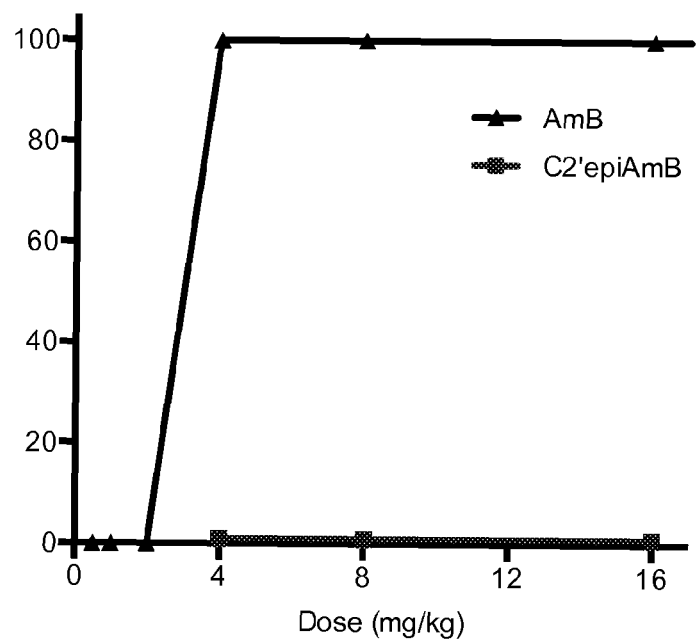
FIG. 8 is a graph depicting lethality in healthy mice resulting from single intravenous administrations in the doses indicated of AmB or C2'epiAmB.

In a separate experiment, acute toxicity was determined by single intravenous administration of AmB or C2'epiAmB to healthy mice, followed by monitoring for lethality. Results are shown in FIG. 8. All mice in the 4 mg/kg AmB dosage group died within seconds. C2'epiAmB was significantly less toxic, with no deaths observed even up to a dose of 16 mg/kg.

REFERENCES CITED (1) Ermishkin, L. N.; Kasumov, K. M.; Potzeluyev, V. M. *Nature* 1976, 262, 698-699.

(2) (a) Monk, B. C.; Goffeau, A. *Science* 2008, 321, 367-369. (b) Cannon, R. D.; Lamping, E.; Holmes, A. R.; Niimi, K.; Tanabe, K.; Niimi, M.; Monk, B. C. *Microbiol.* 2007, 153, 3211-3217.

(3) Mora-Duarte, J.; Betts, R.; Rotstein, C.; Colombo, A. L.; Thompson-Moya, L.; Smietana, J.; Lupinacci, R.; Sable, C.; Kartsonis, N.; Perfect, *J. N. Engl. J. Med.* 2002, 347, 2020-2029.

(4) (a) Johnson, R. H.; Einstein, H. E. *Ann. N.Y. Acad. Sci.* 2007, 1111, 434-441. (b) Schneemann, M.; Imhof, A. *N. Engl. J. Med.* 2005, 352, 410-414.

(5) (a) Walsh, T. J.; Teppler, H.; Donowitz, G. R.; Maertens, J. A.; Baden, L. R.; Dmoszynska, A.; Comely, O. A.; Bourque, M. R.; Lupinacci, R. J.; Sable, C. A.; dePauw, B. E. *N. Engl. J. Med.* 2004, 351, 1391-1402. (b) Walsh, T. J.; Pappas, P.; Winston, D. J.; Lazarus, H. M.; Petersen, F.; Raffalli, J., Yanovich, S.; Stiff, P.; Greenberg, R.; Donowitz, G.; Lee, *J. N. Engl. J. Med.* 2002, 346, 225-234.

(6) Cereghetti, D. M.; Carreira, E. M. Synthesis 2006, 6, 914-942.

(7) (a) Zietse, R.; Zoutendijk, R.; Hoorn, E. J. *Nat. Rev. Nephrol.* 2009, 5, 193-202. (b) Volmer, A. A.; Szpilman A. M.; Carreira, E. M. *Nat. Prod. Rep.* 2010, 27, 1329-1349. (c) Murata, M.; Kasai, Y.; Umegawa, Y.; Matsushita, N.; Tsuchikawa, H.; Matsumori, N.; Oishi, T. *Pure Appl. Chem.* 2009, 81, 1123-1129. (d) Baginski, M.; Resat, H.; Borowski, E. *Biochim. Biophys. Acta* 2002, 1567, 63-78. (e) Bolard, J. *Biochim. Biophys. Acta* 1986, 864, 257-304. (f) de Kruijff, B., Demel, R. A. *Biochim. Biophys. Acta* 1974, 339, 57-70. (g) Andreoli, T. E. *Ann. N.Y. Acad. Sci.* 1974, 235, 448-468.

(8) (a) Gray, K. C.: Palacios, D. S.; Dailey, I.; Endo, M. M.; Uno, B. E.; Wilcock, B. C.; Burke, M. D. *Proc. Natl. Acad. Sci. U.S.A.* 2012, 109, 2234-2239. (b) Palacios, D. S.; Dailey, I.; Siebert, D. M.; Wilcock, B. C.; Burke, M. D. *Proc. Natl. Acad. Sci. U.S.A.* 2011, 108, 6733-6738. (c) Palacios, D. S.; Anderson, T. M.; Burke, M. D. *J. Am. Chem. Soc.* 2007, 129, 13804-13805. (d) Anderson, T. M.; Clay, M. C.; Cioffi, A. G.; Diaz, K. A.; Hisao, G. S.; Tuttle, M. D.; Nieuwkoop, A. J.; Comellas, G.; Maryum, N.; Wang, S.; Uno, B. E.; Wildeman, E. L.; Gonen, T.; Rienstra, C. M.; Burke, M. D. *Nat. Chem.* Bio. 2014, published online Mar. 30, 2014.

(9) (a) Wilcock, B. C.; Endo, M. M.; Uno, B. E.; Burke, M. D. *J. Am. Chem. Soc.* 2013, 135, 8488-91. (b) Uno, B. E.; Endo, M. M.; Struble, J. R; Knapp, D. M.; Burke, M. D. manuscript in progress.

(10) (a) Croatt, M. P.; Carreira, E. M. *Org. Lett.* 2011, 13, 1390-1393. (b) Neumann, A.; Czub, J.; Baginski, M. *J. Phys. Chem. B* 2009, 113, 15875-15885. (c) Matsumori, N.; Sawada, Y.; Murata, M. *J. Am. Chem. Soc.* 2005, 127, 10667-10675. (d) Baran, M.; Mazerski, M. *Biophys. Chem.* 2002, 95, 125-133. (e) Silberstein, A. *J. Membr. Biol.* 1998, 162, 117-126.

(11) Neumann, A.; Baginski, M.; Czub, J. *J. Am. Chem. Soc.* 2010, 132, 18266-18272.

(12) (a) Noguiera, J. M.; Issa, J. P.; Chu, A.-H. A.; Sisel, J. A.; Schum, R. S.; Bennett, C. S. *Eur. J. Org. Chem.* 2012, 2012, 4927-4930. (b) Hou, D.; Lowary, T. L. *Carbohydr. Res.* 2009, 344, 1911-1940. (c) Oberhur, M.; Leimkuhler, C.; Kahne, D. *Org. Lett.* 2004, 6, 2873-2876. (d) Nicolaou, K. C.; Ladduwahetty, T.; Randall, J. L.; Chucholowski, A. *J. Am. Chem. Soc.* 1986, 108, 2466-2467. (e) Overend, W; Rees, C.; Sequeira, J. *J. Chem. Soc.* 1962, 3429-3440.

(13) Wilcock, B. C.; Uno, B. E.; Bromann, G. L.; Clark, M. J.; Anderson, T. M.; Burke, M. D. *Nat. Chem.* 2012, 4, 996-1003.

(14) (a) Nicolaou, K. C.; Daines, R. A.; Chakraborty, T. K.; Ogawa, Y. *J. Am. Chem. Soc.* 1987, 109, 2821-2822. (b) Nicolaou, K. C.; Daines, R. A.; Ogawa, Y.; Chakraborty, T. K. *J. Am. Chem. Soc.* 1988, 110, 4696-4705. (c) Szpilman, A. M.; Manthrope, J. M.; Carreira, E. M. *Angew. Chem. Int. Ed.* 2008, 47, 4339-4342. (d) Szpilman, A. M.; Cereghetti, D. M.; Manthrope, J. M.; Wurtz, N. R.; Carreira, E. M. *Chem. Eur. J.* 2009, 15, 7117-7128.

(15) Guo, H.; O'Doherty, G. A. *Angew. Chem. Int. Ed.* 2007, 46, 5206-5208.

(16) (a) Nicolaou, K. C.; Daines, R. A.; Chakraborty, T. K. *J. Am. Chem. Soc.,* 1987, 109, 2208-2210. (b) Nicolaou, K. C.; Chakraborty, T. K.; Ogawa, Y.; Daines, R. A.; Simpkins, N. S.; Furst, G. T. *J. Am. Chem. Soc.,* 1988, 110, 4660-4672. (c) Nicolaou, K. C.; Daines, R. A.; Chakraborty, T. K.; Ogawa, Y. *J. Am. Chem. Soc.,* 1988, 110, 4685-4696.

(17) (a) Sundar, S.; Jha, T. K.; Thakur, C. P.; Sinha, P. K.; Bhattacharya, S. K. *N. Engl. J. Med.* 2007, 356, 2571-2581. (b) Zager, R. A. *Am. J. Kidney. Dis.* 2000, 36, 238-249. (c) Sawaya, B. P.; Briggs, J. P; Schnerrmann, J. *J. Am. Soc. Nephrol.* 1995, 6, 154-164. (d) Keim, G. R.; Poutsiaka, J. W.; Kirpan, J.; Keysser, C. H. *Science* 1973, 179, 584-585.

(18) Due to the limited solubility of AmB and its derivatives in the renal cell media, 80 μM is the highest concentration we were able to study. At higher concentrations, the aggregate blocks the light path of the plate reader, giving false high absorbance readings. However, microscope images of the renal cells after treatment with AmdeB and C2'deOAmB at concentrations even up to 200 μM revealed no visual evidence of toxicity.

(19) (a) Fowler, B. S.; Laemmerhold, K. M.; Miller, S. J. *J. Am. Chem. Soc.* 2012, 134, 9755-9761. (b) Duggan, K. C.; Hermanson, D. J.; Musee, J.; Prusakiewicz, J. J.; Scheib, J. L.; Carter, B. D.; Banerjee, S.; Oates. J. A.; Marnett, L. *J. Nat. Chem. Biol.* 2011, 7, 803-809. (c) Hendriks, B. S.; Seidl, K. M.; Chabot, J. R. *BMC Syst. Biol.* 2010, 4, 23-39. (d) Neant-Fery, M.; Garcia-Ordonez, R. D.; Logan, T. P.; Selkoe, D. J.; Li, L.; Reinstatler, L.; Leissring, M. A. *Proc. Natl. Acad. Sci.* 2008, 105, 9582-9587. (e) Knight, Z. A.; Shokat, K. M. *Chem. Biol.* 2005, 12, 621-637. (f) Koike, K.; Oleschuk, C. J.; Haimeur, A.; Olsen, S. L.; Deeley, R. G.; Cole, S. P. C. *J. Biol. Chem.* 2002, 277, 49495-49503. (g) Changeux, J. P.; Edelstein, S. J. *Neuron* 1998, 21, 959-980.

(20) (a) Ganis, P.; Avitabile, G.; Mechlinski, W.; Schaffner, C. P. *J. Am. Chem. Soc.* 1971, 93, 4560-4564. (b) Jarzembska, K. N.; Kaminski, D.; Hoser, A. A.; Malinska, M.; Senczyna, B.; Wozniak, K.; Gagos, M. *Cryst. Growth Des.* 2012, 12, 2336-2345.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All patents and published patent applications mentioned in the description above are incorporated by reference herein in their entirety.

We claim:
1. C2'epiAmB, represented by

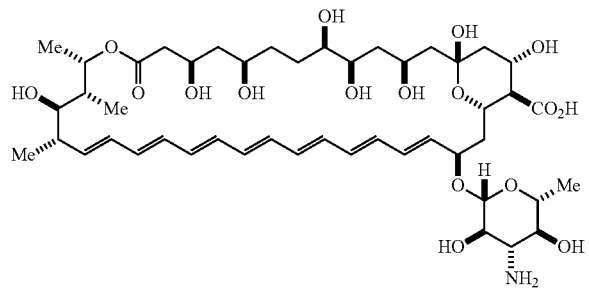

or a pharmaceutically acceptable salt thereof.

2. A pharmaceutical composition, comprising the compound of claim 1; and a pharmaceutically acceptable carrier.

3. A method of inhibiting growth of a yeast or fungus, comprising contacting the yeast or fungus with an effective amount of C2'epiAmB, represented by

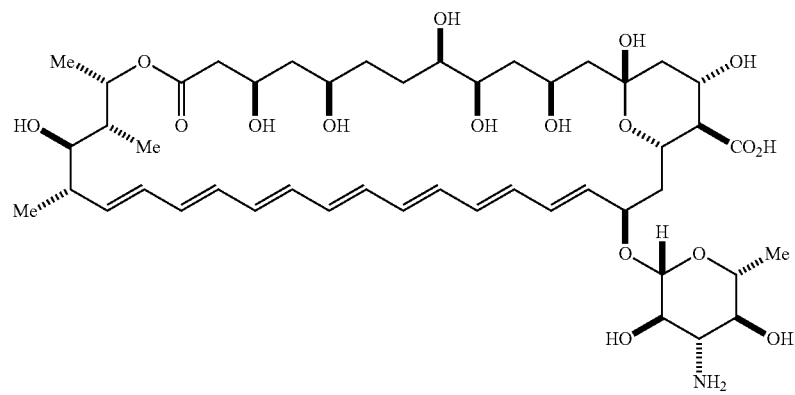

or a pharmaceutically acceptable salt thereof.

4. A method of treating a yeast or fungal infection, comprising administering to a subject in need thereof a therapeutically effective amount of C2'epiAmB, represented by

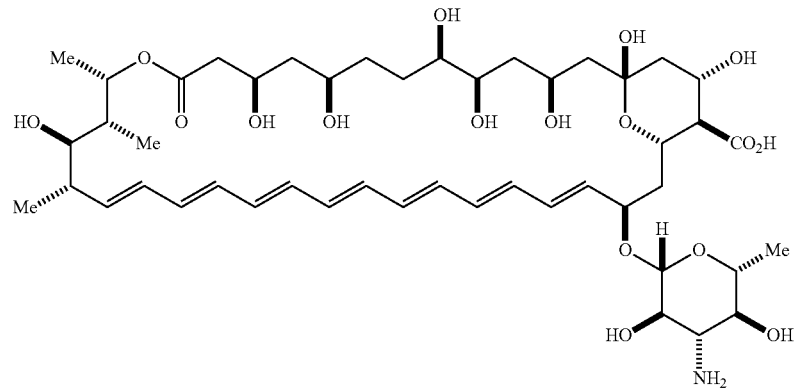

or a pharmaceutically acceptable salt thereof.

5. The method of claim 4, wherein the administration is topical.

6. The method of claim 4, wherein the administration is systemic.

7. The method of claim 4, wherein the administration is oral.

8. The method of claim 4, wherein the administration is intravenous.

9. The method of claim 4, wherein the administration is intramuscular.

* * * * *